United States Patent
Sasaki

(10) Patent No.: US 11,603,560 B2
(45) Date of Patent: Mar. 14, 2023

(54) PARTICLE MEASURING METHOD, PARTICLE MEASURING APPARATUS, AND NUCLEIC ACID CONCENTRATION MEASURING SYSTEM

(71) Applicant: CANON KABUSHIKI KAISHA, Tokyo (JP)

(72) Inventor: Toru Sasaki, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 908 days.

(21) Appl. No.: 16/450,648

(22) Filed: Jun. 24, 2019

(65) Prior Publication Data

US 2020/0002757 A1    Jan. 2, 2020

(30) Foreign Application Priority Data

Jun. 29, 2018    (JP) .............................. JP2018-125435

(51) Int. Cl.
*G06T 7/00*    (2017.01)
*C12Q 1/6851*    (2018.01)

(52) U.S. Cl.
CPC .......... *C12Q 1/6851* (2013.01); *G06T 7/0012* (2013.01); *G06T 2207/10064* (2013.01); *G06T 2207/30072* (2013.01)

(58) Field of Classification Search
None
See application file for complete search history.

(56) References Cited

U.S. PATENT DOCUMENTS

| | | | | |
|---|---|---|---|---|
| 5,720,928 | A * | 2/1998 | Schwartz ......... | G01N 27/44773 422/186 |
| 6,610,256 | B2 * | 8/2003 | Schwartz ............... | C12Q 1/683 422/186 |
| 9,322,055 | B2 | 4/2016 | Janaway | |
| 10,429,302 | B2 * | 10/2019 | Nolan ................ | G01N 15/1429 |
| 10,557,174 | B2 * | 2/2020 | Janaway .............. | C12Q 1/6886 |
| 2003/0036067 | A1 * | 2/2003 | Schwartz .......... | G01N 27/44773 435/6.12 |
| 2004/0197791 | A1 * | 10/2004 | Makarov ................. | C12Q 1/686 435/6.14 |
| 2014/0227682 | A1 * | 8/2014 | Seth ....................... | G06T 7/0012 435/5 |
| 2017/0045451 | A1 * | 2/2017 | Nolan .............. | G01N 33/56983 |
| 2019/0292594 | A1 * | 9/2019 | Rigatti ................. | C12Q 1/6874 |

OTHER PUBLICATIONS

I. Cao, et al., "Advances in digital polymerase chain reaction (dPCR) and its emerging biomedical applications", Biosensors and Bioelectronics, vol. 90, pp. 459-474 (2017).
U.S. Appl. No. 16/452,232, filed Jun. 25, 2019, by Toru Sasaki.

* cited by examiner

*Primary Examiner* — Tsung Yin Tsai
(74) *Attorney, Agent, or Firm* — Venable LLP

(57) ABSTRACT

Provided is a particle measuring method for measuring, based on image data containing an image of a plurality of particles, a size of each of the particles included in the image data. The particle measuring method includes: acquiring a position of each of the plurality of particles from the image data; extracting two particles vicinal to each other; and calculating the size of each of the particles based on a distance between the two vicinal particles.

8 Claims, 20 Drawing Sheets

FIG. 6A

NODE TABLE 130

| NODE NO. | WHITE AREA NO. | PARTICLE POSITION |
|---|---|---|
| 0 | 1 | x1, y1 |
| 1 | 3 | x3, y3 |
| 2 | 4 | x4, y4 |
| 3 | 7 | x7, y7 |
| 4 | 8 | x8, y8 |
| 5 | 11 | x11, y11 |
| 6 | 13 | x13, y13 |
| 7 | 14 | x14, y14 |
| 8 | 17 | x17, y17 |

FIG. 6B

EDGE TABLE 135

| EDGE NO. | SMALL NODE NO. | LARGE NODE NO. |
|---|---|---|
| 0 | 0 | 1 |
| 1 | 0 | 2 |
| 2 | 1 | 2 |
| 3 | 1 | 4 |
| 4 | 2 | 6 |
| 5 | 3 | 4 |
| 6 | 4 | 5 |
| 7 | 4 | 6 |
| 8 | 6 | 7 |
| 9 | 6 | 8 |

FIG. 9A

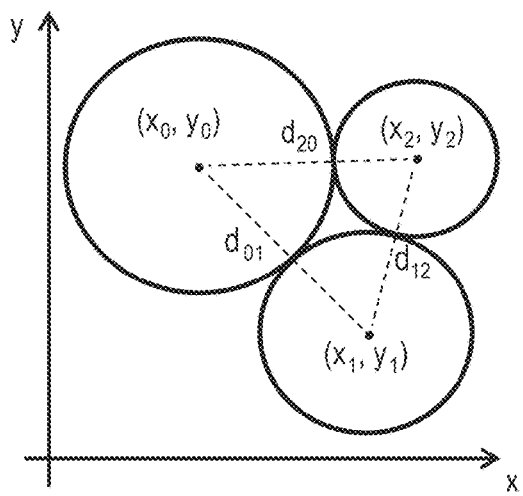

FIG. 9B

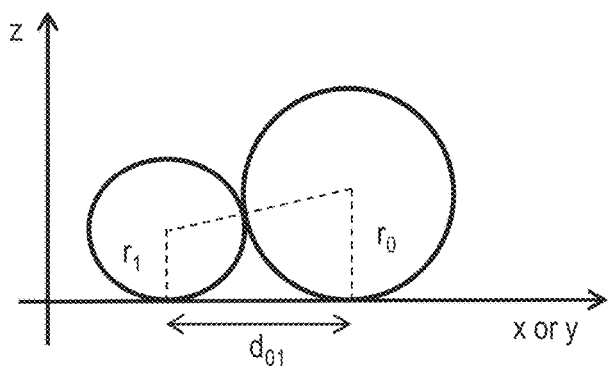

FIG. 9C

SIMULTANEOUS EQUATION 150

$$\begin{pmatrix} \log d_{01}^2/4 \\ \log d_{02}^2/4 \\ \log d_{12}^2/4 \\ \vdots \\ \log d_{pn}^2/4 \end{pmatrix} = \begin{pmatrix} 1 & 1 & 0 & & \\ 1 & 0 & 1 & \cdots & \\ 0 & 1 & 1 & & \\ & \vdots & & \ddots & \\ & & & & 1 \end{pmatrix} \begin{pmatrix} \log r_0 \\ \log r_1 \\ \log r_2 \\ \vdots \\ \log r_n \end{pmatrix}$$

FIG. 9D

SIMULTANEOUS EQUATION 151

$$\begin{pmatrix} d_{01} \\ d_{02} \\ d_{12} \\ \vdots \\ d_{pn} \end{pmatrix} = \begin{pmatrix} 1 & 1 & 0 & & \\ 1 & 0 & 1 & \cdots & \\ 0 & 1 & 1 & & \\ & \vdots & & \ddots & \\ & & & & 1 \end{pmatrix} \begin{pmatrix} r_0 \\ r_1 \\ r_2 \\ \vdots \\ r_n \end{pmatrix}$$

FIG. 11

| | CONCENTRATION ESTIMATING METHOD | POSITIVE RATIO (%) | TARGET VALUE (copies/ul) | AVERAGE ESTIMATE VALUE (copies/ul) | STANDARD DEVIATION (copies/ul) | AVERAGE VALUE ERROR RATIO (%) | 95% CONFIDENCE INTERVAL RATIO (%) |
|---|---|---|---|---|---|---|---|
| COMPARATIVE EXAMPLE 1 | POISSON DISTRIBUTION METHOD | 1 | 86.6 | 86.8 | 1.1 | 0.3 | 2.4 |
| COMPARATIVE EXAMPLE 2 | POISSON DISTRIBUTION METHOD | 10 | 887.2 | 869.6 | 19.0 | -2.0 | 4.2 |
| COMPARATIVE EXAMPLE 3 | POISSON DISTRIBUTION METHOD | 50 | 5837.0 | 5218.2 | 101.2 | -10.6 | 3.4 |
| COMPARATIVE EXAMPLE 4 | WEIGHTED AVERAGING METHOD | 1 | 86.6 | 89.7 | 19.0 | 3.6 | 42.9 |
| COMPARATIVE EXAMPLE 5 | WEIGHTED AVERAGING METHOD | 10 | 887.2 | 902.7 | 64.9 | 1.7 | 14.3 |
| COMPARATIVE EXAMPLE 6 | WEIGHTED AVERAGING METHOD | 50 | 5837.0 | 5794.4 | 240.2 | -0.7 | 8.1 |

FIG. 14

| | CONCENTRATION ESTIMATING METHOD | POSITIVE RATIO (%) | TARGET VALUE (copies/ul) | AVERAGE ESTIMATE VALUE (copies/ul) | STANDARD DEVIATION (copies/ul) | AVERAGE VALUE ERROR RATIO (%) | 95% CONFIDENCE INTERVAL RATIO (%) |
|---|---|---|---|---|---|---|---|
| EXAMPLE 1 | COUNTING STEP S161 | 1 | 86.6 | 86.3 | 2.4 | -0.3 | 5.4 |
| EXAMPLE 2 | COUNTING STEP S161 | 10 | 887.2 | 879.1 | 18.2 | -0.9 | 4 |
| EXAMPLE 3 | COUNTING STEP S161 | 50 | 5837 | 5869.9 | 188.1 | 0.6 | 6.3 |

PARTICLE MEASURING METHOD, PARTICLE MEASURING APPARATUS, AND NUCLEIC ACID CONCENTRATION MEASURING SYSTEM

BACKGROUND OF THE INVENTION

Field of the Invention

The present invention relates to a particle measuring method, a particle measuring apparatus, and a nucleic acid concentration measuring system.

Description of the Related Art

For example, in identification of the cause of a disease and determination of cancer treatment policy, the use of measurement of a concentration of target nucleic acids is advancing. As a measuring method, there has been actively developed a combination of a polymerase chain reaction (PCR) method involving amplifying the number of nucleic acids and a fluorescence probe configured to emit fluorescence when being bound to the target nucleic acid. However, under the actual circumstances, the measurement accuracy of this method is insufficient for medical application.

In general, a concentration of a fluorescent pigment (that is, a concentration of the target nucleic acids) is measured based on a fluorescence intensity. However, the fluorescence intensity is low, and hence gradation cannot be accurately measured. The reproducibility of an amplification ratio of the number of nucleic acids by the PCR method is not high, and hence the measurement accuracy is not improved even with measurement after amplification of the fluorescence intensity (number of nucleic acids). In this situation, there has been widely utilized a method (real-time PCR method) involving creating a reference by applying the PCR method to nucleic acids having a known concentration under the same environment as that of the target nucleic acids. The real-time PCR method achieves high accuracy among procedures for measuring gradation of the fluorescence intensity, but creation of a reference or other such processing is complicated. Thus, there is a problem in that the difference from the amplification ratio of the reference remains as an estimation error.

As a solution to the above-mentioned problem, there has been known a digital PCR (hereinafter referred to as "dPCR") method, in which the measurement of gradation of the fluorescence intensity is not required. In the dPCR method, a solution containing target nucleic acids is divided into a large number of small sections, and the presence or absence of fluorescent emission is examined by performing the PCR method in each of the sections. The concentration of the target nucleic acids is estimated based on a ratio of the number of sections in which fluorescence is not emitted to the total number of sections.

As described in L. Cao et al., "Advances in digital polymerase chain reaction (dPCR) and its emerging biomedical applications", Biosensors and Bioelectronics, vol. 90, pages 459-474 (2017), there have been proposed a large number of nucleic acid concentration measuring apparatus based on the dPCR method. Of those, a method utilizing, as small sections, a large number of small liquid droplets generated in oil is advantageous for reduction in running cost and downsizing, and hence is now mainstream. In the method utilizing the liquid droplets as small sections, the concentration of target nucleic acids is estimated through use of a Poisson distribution, and the above-mentioned estimating method is based on the premise that the size of each of the liquid droplets is the same.

When the sizes of liquid droplets are varied, the number of liquid droplets that can be used for measurement is reduced, with the result that the estimation accuracy of the concentration of target nucleic acids is decreased. In U.S. Pat. No. 9,322,055, there is disclosed a dPCR method, which includes the step of measuring the volume of each small section, and can be applied to the case in which the volumes of the liquid droplets are not constant.

In a dPCR-type concentration measuring apparatus utilizing liquid droplets as small sections, it is desired that a period of time to be taken for generation of the liquid droplets be shortened. In the related art, the number of liquid droplets is about 20,000, and in the future, a further increase in number of liquid droplets is expected in order to enhance the accuracy of an apparatus and widen a dynamic range. In general, when a liquid droplet generation speed is increased, the sizes of liquid droplets are liable to be varied. The target nucleic acid concentration estimation utilizing the Poisson distribution is based on the premise that the sizes of liquid droplets are uniform. This requirement is considered to be satisfied by correcting a concentration estimate value by measuring each liquid droplet volume as in the method disclosed in U.S. Pat. No. 9,322,055.

However, when the number of liquid droplets is increased (that is, the number of sections for dividing the solution is increased), and the diameter of each of the liquid droplets is decreased, the depth of field of an image pickup lens to be used for imaging the liquid droplets strongly influences the measurement results of liquid droplet volumes. As an example, there is given a case in which a specimen (entire solution to be measured) has a volume of 20 μL, and the number of liquid droplets is 50,000. When it is assumed that the average diameter of the liquid droplets is about 90 μm, and the liquid droplets are closely arranged on a two-dimensional plane, the image pickup range is 25 mm×25 mm. In this case, the liquid droplets are arranged so closely as to be brought into contact with each other. Therefore, when the liquid droplets are imaged through use of an image pickup lens having a depth of field of 50 μm or more, contours of the liquid droplets vicinal to each other overlap with one another, and it thus becomes difficult to identify a boundary. As a result, it becomes impossible to measure the volumes of the liquid droplets. In such a case, the method disclosed in U.S. Pat. No. 9,322,055 cannot be applied.

The volumes can be measured by suppressing the influence of blurring of the contours of the liquid droplets, but in this case, it is required to set the depth of field to about 9 μm (one tenth of an average diameter), that is, to increase the enlargement magnification of the image pickup lens to 10 times or more. The image pickup range is 25 mm×25 mm, and hence it is required to pick up about 100 images even through use of a camera equipped with a full-size image sensor (36 mm×24 mm). Stage movement and autofocusing are required, and hence there also arise new problems of an increase in apparatus price and a complicated configuration of the apparatus.

In view of the foregoing, there is a demand for a measuring method capable of accurately measuring a size of a particle even under a state in which the contours of minute particles cannot be accurately obtained from image data due to the influence of the blurring and the depth of field of an image pickup lens or the influence of the arrangement of the minute particles.

SUMMARY OF THE INVENTION

The present invention has been made in view of the above-mentioned circumstances, and an object of the present invention is to provide a particle measuring method, which achieves measurement of a size of a minute particle based on contour information on the minute particle obtained from an image having a low resolution or an image having an unclear contour.

In order to solve the above-mentioned problem, a particle measuring method according to at least one embodiment of the present invention is a method of measuring, based on image data containing an image of a plurality of particles, a size of each of the plurality of particles included in the image data. The method includes: acquiring a position of each of the plurality of particles from the image data; extracting two particles vicinal to each other; and calculating the size of each of the plurality of particles based on a distance between the vicinal two particles.

According to at least one embodiment of the present invention, it is possible to measure the size of a minute particle based on contour information on the minute particle obtained from the image having a low resolution or the image having an unclear contour.

Further features of the present invention will become apparent from the following description of exemplary embodiments with reference to the attached drawings.

BRIEF DESCRIPTION OF THE DRAWINGS

FIG. 6A is an exemplary node table for showing data of a vicinal particle graph.

FIG. 6B is an exemplary edge table for showing data of the vicinal particle graph.

FIG. 9A is a graph for showing one example of a simultaneous equation to be used for estimating a size of each of the particles and showing one example of spheres observed from a direction perpendicular to a two-dimensional plane on which the spheres are arranged.

FIG. 9B is a graph for showing one example of a simultaneous equation to be used for estimating a size of each of the particles and showing one example of spheres observed from a direction that is parallel to the plane on which the spheres are arranged and is perpendicular to a plane including a contact point between the spheres and each center of the spheres.

FIG. 9C is an exemplary simultaneous equation in a case where a particle radius difference is large.

FIG. 9D is an exemplary simultaneous equation in a case where the particle radius difference can be ignored.

FIG. 11 is a table for showing results of simulation for verifying estimation accuracy of a Poisson distribution method and a weighted averaging method as Comparative Examples.

FIG. 14 is a table for showing one example of results obtained by verifying estimation accuracy of the counting step in the target nucleic acid counting method in at least one embodiment of the present invention.

DESCRIPTION OF THE EMBODIMENTS

The overview of a particle measuring method and a target nucleic acid counting method according to at least one embodiment of the present invention is described. The present invention is not limited thereto.

[Particle Measuring Method]

Now, the particle measuring method according to at least one embodiment of the present invention is described with reference to the drawings.

<Object to be Measured by Particle Measuring Method>

First, an object to be measured by the particle measuring method according to at least one embodiment is described. Particles to be measured by the particle measuring method refer to, for example, liquid droplets, an emulsion, or a gel generated by dividing a solution containing target nucleic acids each having a particular base sequence. The size of each particle to be measured represents a volume, a sectional area, and a diameter or radius of a particle having a shape close to a spherical shape or a sphere containing one particle (hereinafter referred to as "particle-including sphere"). For convenience of description of calculation, the above-mentioned spherical particle or particle-including sphere is sometimes referred to as "particle". The particle measuring method according to at least one embodiment achieves measurement of, based on image data on a specimen including a plurality of such particles, a size of each of the particles included in the image data.

<Image Data to be Handled by Particle Measuring Method>

Figure 1A:
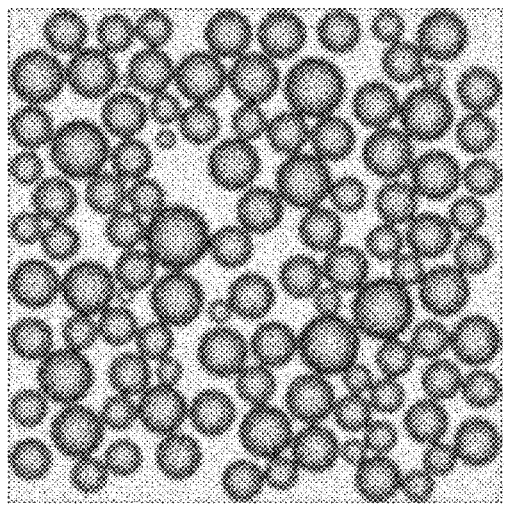
FIG. 1A is a view for illustrating features of image data containing particles, in which an image of the image data is obtained by arranging particles in a petri dish containing oil, irradiating the petri dish with illumination light from a lower surface thereof, and imaging the particles from above.
Figure 1B:
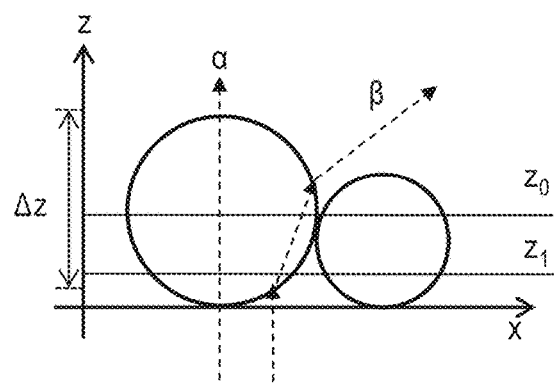
FIG. 1B is a graph for showing an example of particle surfaces and a light beam in a cross section parallel to an optical axis.
Figure 1C:
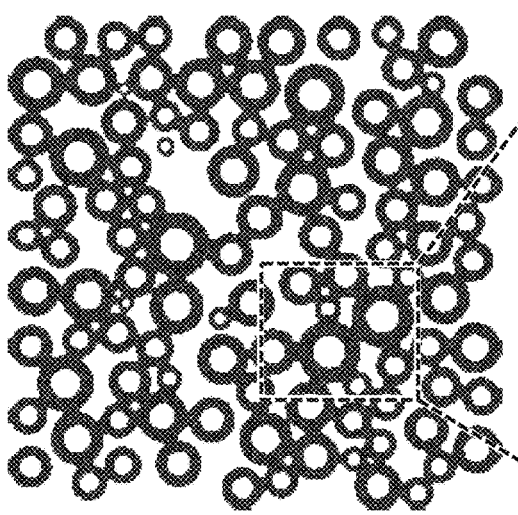
FIG. 1C is a view for illustrating binary image data generated by assigning two kinds of pixel values representing a light/dark state to the image of the particles.
Figure 1D:
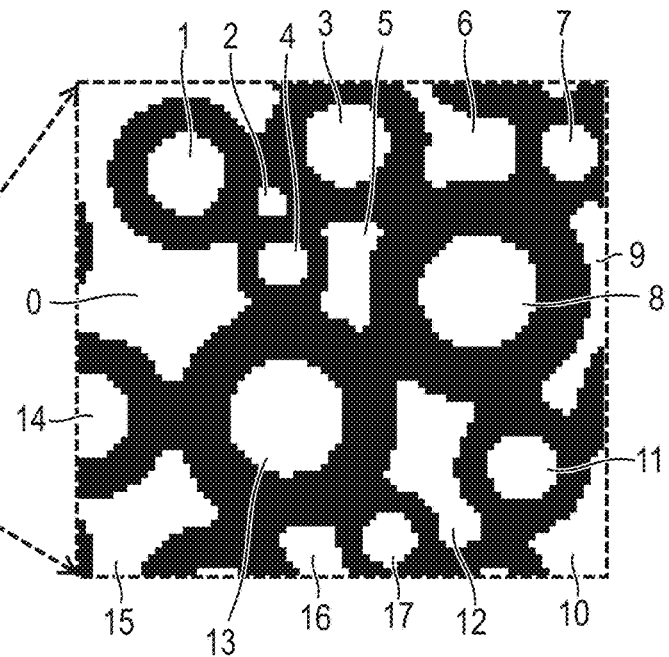
FIG. 1D is a view for illustrating an example in which an area division step is applied to a partial area of the binary image data illustrated in FIG. 1C.

The way of understanding image data to be used in the particle measuring method according to at least one embodiment is described with reference to FIG. 1A to FIG. 1D. FIG. 1A, FIG. 1C, and FIG. 1D are each a view for illustrating features of the image data containing particles, and FIG. 1B is a graph for showing features of the image data containing particles. FIG. 1A is a view for illustrating an image obtained by arranging particles in a petri dish containing oil, irradiating the petri dish with illumination light from a lower surface thereof, and imaging the particles from above. FIG. 1B is a graph for showing an example of particle surfaces and a light beam in a cross section parallel to an optical axis. FIG. 1C is a view for illustrating binary image data generated by assigning two kinds of pixel values representing a light/dark state to the image of the particles. FIG. 1D is a view for illustrating an example in which an area division step is applied to a partial area of the binary image data illustrated in FIG. 1C.

Such image data as illustrated in FIG. 1A is hereinafter referred to as "particle image data". It is understood from the particle image data that a density difference occurs in a center portion and a peripheral portion of each of the particles. The density difference is caused by the following. As illustrated in FIG. 1B, a light beam "α" passing through the center portion of the particle reaches an entrance pupil of a camera without being refracted, whereas a light beam "β" passing through the peripheral portion of the particle does not reach the entrance pupil due to refraction and total reflection. Thus, the density difference occurs.

A boundary between a dark pixel area in the peripheral portion of the particle and a light pixel area corresponding to the oil outside of the particle illustrated in FIG. 1A does not match a circle having the same diameter as that of the particle. For example, when the depth of field of an image pickup lens is represented by $\Delta z$ of FIG. 1B, an image sensor of the camera receives light under a state in which light distributions of cross sections (for example, "$z_0$" and "$z_1$") within the range of $\Delta z$ are added. A circular light distribution having a diameter close to a particle diameter is formed in the cross section "$z_0$", whereas a light distribution having a small diameter is formed in the cross section "$z_1$". When those light distributions are added, a circle having a diameter smaller than the particle diameter is formed.

The cross sections $z_0$ and $z_1$ are not Lambertian surfaces, and hence the above-mentioned description is not strictly exact. To be exact, a height "z" of an object surface is varied for each light beam, and a light beam reaches a pixel at a position on the image sensor corresponding to an intersection "x" between the object surface "z" and the light beam, with the result that a light intensity is added. When there is a vicinal particle, a complicated distribution is formed also through, for example, multiple reflection of the particle surface. Thus, under the situation in which the depth of field of the image pickup lens is large, and the particles are vicinal to each other, it is difficult to accurately obtain contour information from the particle image data.

In the particle measuring method according to at least one embodiment, separately from the particle image data, binary image data, which is generated by assigning two kinds of pixel values representing a light/dark state to the image of the particles as illustrated in FIG. 1C, is used. Any values can be selected as the two pixel values to be used in the image data. A light state is represented by a white color, and a dark state is represented by a black color. An area formed of a pixel in the light state and an area formed of a pixel in the dark state are referred to as "white area" and "black area", respectively. In the image data illustrated in FIG. 1C, a center portion of each of the particles and an interparticle area therebetween correspond to the white area represented by a white pixel, and a peripheral portion of each of the particles and an interparticle area therebetween correspond to the black area represented by a black pixel.

The particle image data illustrated in FIG. 1A was imaged through use of transmitted illumination. Alternatively, for example, the following method can also be performed: particles mixed with a coloring matter are illuminated, and scattered light from the particles are picked up. In this case, the density difference of the center portion and peripheral portion of each of the particles is eliminated, with the result that the entire particle becomes light, and the pixel corresponding to the oil between the particles becomes dark. The association relation between the density difference distribution and the particles and oil are changed, but the detection of a contour of each of the particles is difficult in the same manner as in the case of transmitted illumination. The association relation between the light/dark state and the particles and oil is changed also in the binary image, but this change does not influence the performance of a particle position acquisition step described later. Therefore, at least one embodiment of the present invention can also be applied to the above-mentioned pickup of scattered light.

<Flow of Entire Particle Measuring Method>

Figure 2:
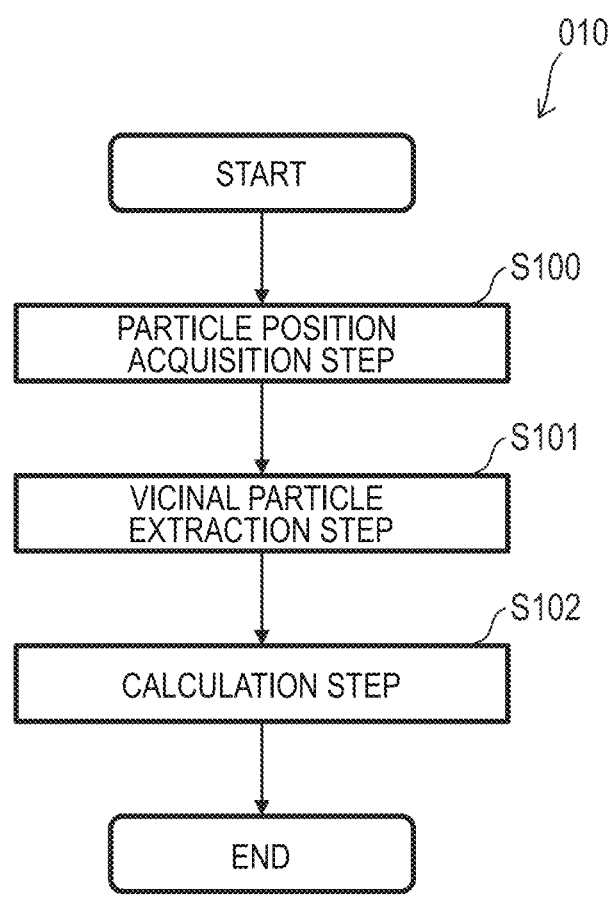
FIG. 2 is a flowchart for illustrating one example of a processing procedure of a particle measuring method according to at least one embodiment of the present invention.

The procedure of a particle measuring method 010 according to at least one embodiment of the present invention is described with reference to FIG. 2. FIG. 2 is a flowchart for illustrating one example of a processing procedure of the particle measuring method 010 according to at least one embodiment.

A particle position acquisition step S100 is a step of acquiring positional data on each particle from particle image data. In this case, the positional data on each particle refers to coordinate values corresponding to the center of each particle in a coordinate system in the particle image data or in a coordinate system on an object surface or an image surface.

A vicinal particle extraction step S101 is a step of extracting two particles vicinal to each other from a plurality of particles. The detail of the vicinal particle extraction step S101 is described later.

A calculation step S102 is a step of calculating a distance between the two vicinal particles based on the positional data, and solving a simultaneous equation based on the distance to calculate a size of each of the particles.

<Particle Position Acquisition Step in Particle Measuring Method>

Figure 3:
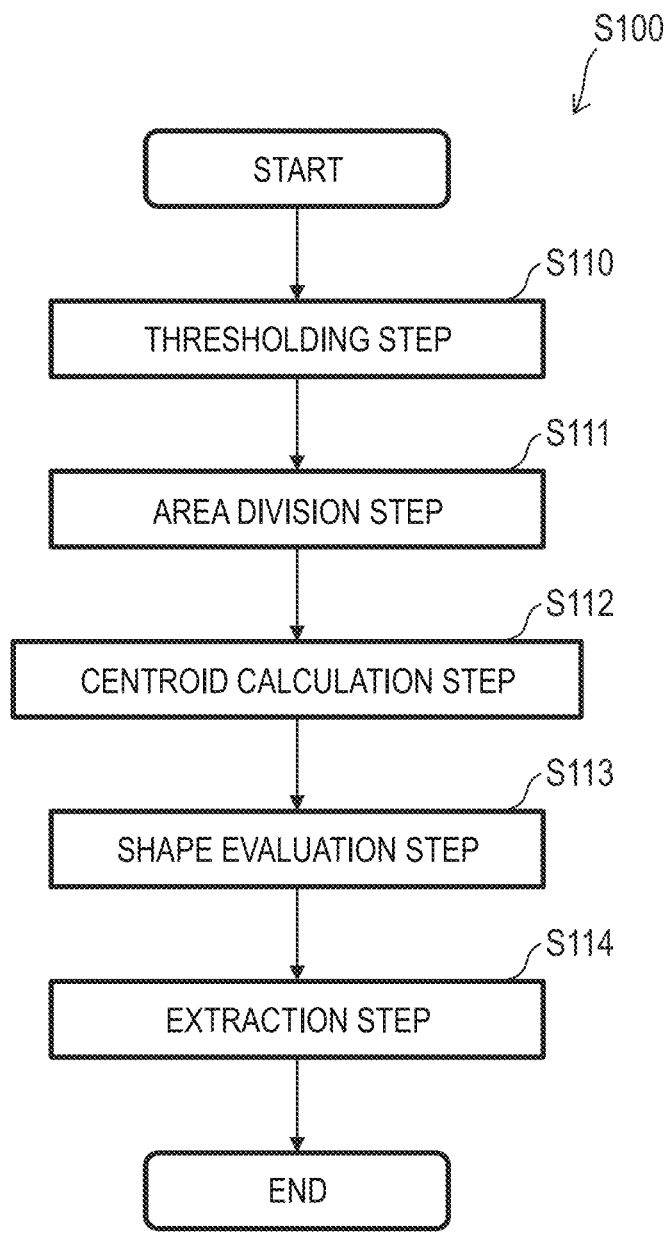
FIG. 3 is a flowchart for illustrating one example of a processing procedure of a particle position acquisition step in the particle measuring method according to at least one embodiment of the present invention.

One example of a processing procedure of the particle position acquisition step S100 is described with reference to FIG. 3. FIG. 3 is a flowchart for illustrating one example of the processing procedure of the particle position acquisition step S100 in the particle measuring method 010 according to at least one embodiment of the present invention. In this procedure, the particle image data is input through transmitted illumination illustrated in FIG. 1A. However, this procedure is applicable also to another kind of particle image data, which is generated, for example, through reception of scattered light from a coloring matter by changing an evaluation value of a shape evaluation step S113 described later.

A thresholding step S110 is a step of generating binary image data from particle image data. In this case, pixels are classified into a white pixel representing a center portion of each of the particles and an interparticle area therebetween and a black pixel representing a peripheral portion of each of the particles and an interparticle area therebetween.

An area division step S111 is a step of grouping the white area of the binary image data. For example, when the area division step S111 is applied to a partial area of the binary image data illustrated in FIG. 1C, there are eighteen white area groups, and numbers of from 0 to 17 are assigned to the respective white area groups, as illustrated in FIG. 1D.

A centroid calculation step S112 is a step of calculating a centroid ($x_w$, $y_w$) given by Expression 1 below for each of the white area groups.

$$x_w = \frac{\sum_{i=0}^{n-1} x_i}{n}, \quad y_w = \frac{\sum_{i=0}^{n-1} y_i}{n} \qquad \text{(Expression 1)}$$

In Expression 1, "$x_i$" and "$y_i$" (i=0, . . . n−1) represent coordinate values of a pixel forming one white area group. Thus, the centroid position of pixels in the particle area can be determined as a particle position.

Figure 4:
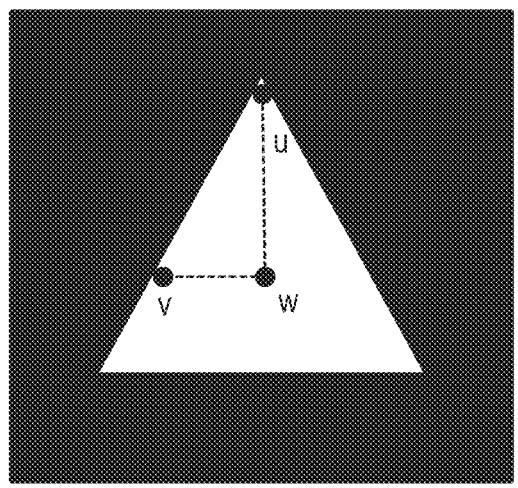
FIG. 4 is a view for illustrating one example of shape evaluation in a shape evaluation step.

In the shape evaluation step S113, a shape evaluation value is determined for each of the white area groups. As an example of the shape evaluation value, a flatness is described with reference to FIG. 4. FIG. 4 is a view for illustrating one example of shape evaluation in the shape evaluation step S113. The flatness is a value representing a flattening degree of the white area. When the flatness is close to 0, the area is close to a circle. As the value of the flatness is increased, unevenness becomes larger. As illustrated in FIG. 4, in calculation of a flatness, a distance from a centroid "w" of a white area group of interest to a pixel located at an endmost position is determined by following a plurality of directions. In this example, a pixel at an end along the upper direction is "u", and a pixel at an end in the left direction is "v". A distance between "u" and "w", and a distance between "v" and "w" are determined. When a maximum value in the obtained distances is represented by "$d_L$" and a minimum value therein is represented by "$d_S$", a flatness L is given by Expression 2 below.

$$L = 1 - \frac{d_S}{d_L} \qquad \text{(Expression 2)}$$

In the case of a white area that is greatly curved as in a white area group 0 illustrated in FIG. 1D, the centroid may be located outside the white area in some cases. The centroid of the white area group 0 is located in the vicinity of the white area group 1, and hence there is no constituent pixel of the white area group 0 even when such a pixel is searched for along the right direction. In such case, a pixel at an end closer to the centroid along the opposite direction is determined, and a negative sign is assigned to the distance.

There may be a plurality of kinds of shape evaluation values. For example, the number of pixels forming a white area group, and an average value or a standard deviation of distances from a centroid to constituent pixels can be used.

In an extraction step S114, a white area group corresponding to a particle is extracted based on the shape evaluation value. The white area group of the particle is not always a perfect circle, and hence it is difficult to directly extract the white area group based on a flatness. However, white areas other than the particles can be easily excluded through use of the shape evaluation value to leave the white area corresponding to the particle by an eliminating method. For example, the flatness of the white area group 0 illustrated in FIG. 1D is a value close to 1 and can be excluded as an area other than the particle. In addition, the number of pixels belonging to the white area group 2 is obviously smaller than that of the white area of the particle, and hence can be excluded. Thus, a particle area that is a partial area representing a center portion of the particle can be extracted. With the foregoing, the number of the white area group corresponding to the particle, and the centroid position that is positional data can be obtained. According to the above-mentioned procedure, the position of the particle included in the image data can be accurately acquired.

<Vicinal Particle Extraction Step in Particle Measuring Method>

Figure 5A:
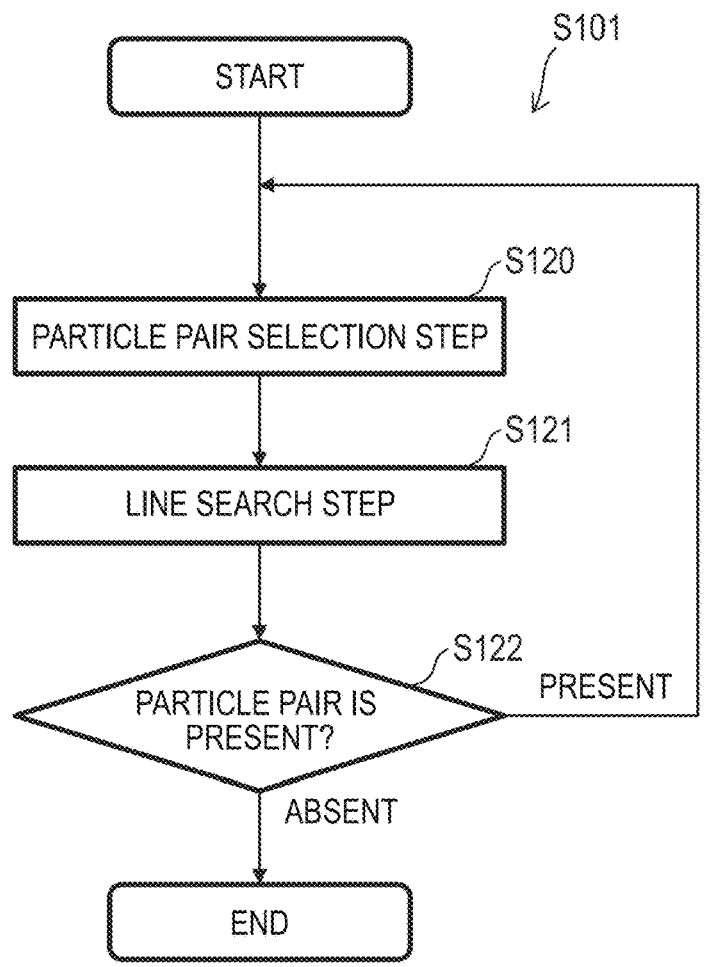
FIG. 5A is a flowchart for illustrating one example of a processing procedure of a vicinal particle extraction step in a case where a white area between the particles can be detected.
Figure 5B:
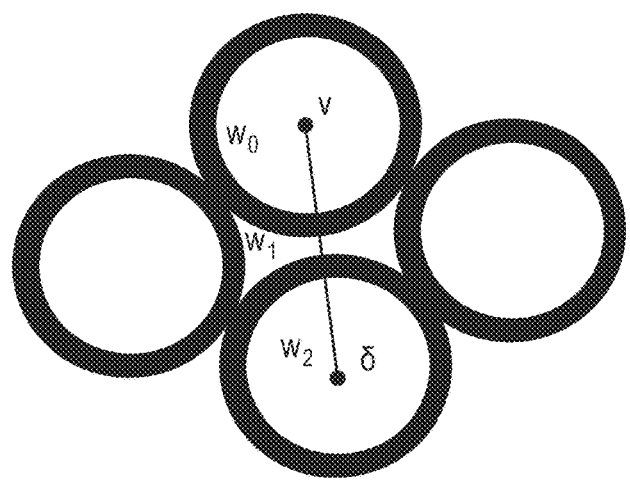
FIG. 5B is a view for illustrating one example of a relationship between the white area and a black area in a binary image in the case where the white area between the particles can be detected.

One example of a processing procedure of the vicinal particle extraction step S101 is described with reference to FIG. 5A and FIG. 5B. FIG. 5A and FIG. 5B are a flowchart and a view, respectively, for illustrating one example in a case where there is a white area between particles. FIG. 5A is a flowchart for illustrating one example of the processing procedure of the vicinal particle extraction step S101. FIG. 5B is a view for illustrating one example of a relationship between a white area and a black area in a binary image. When particle image data is acquired through use of an image pickup lens having a small depth of field and transmitted illumination, such a binary image as illustrated in FIG. 5B is obtained.

A particle pair selection step S120 is a step of selecting two particle white areas having a small distance therebetween (having a small difference in positional data) from white area groups corresponding to particles (hereinafter referred to as "particle white areas") obtained in the particle position acquisition step S100. In FIG. 5B, it is assumed that particle white areas "$w_0$" and "$w_2$" are selected.

In a line search step S121, white area groups, to which pixels located on a straight line connecting center positions (coordinates corresponding to positional data) of the two selected particle white areas belong, are examined in the binary image. When there are no pixels belonging to white area groups other than the two particle white areas, it is determined that the two particles are vicinal to each other. In FIG. 5B, the center positions of the particle white areas "$w_0$" and "$w_2$" are "γ" and "δ", respectively, and white pixels on the straight line connecting "γ" and "δ" to each other belong also to a white area group "$w_1$", and hence it is determined that the two particles are not vicinal to each other.

The white area groups determined to be vicinal to each other in the line search step S121 are registered in such tables each expressing a graph structure as shown in FIG. 6A and FIG. 6B. FIG. 6A and FIG. 6B are each a table for showing data of a vicinal particle graph. FIG. 6A is a table for showing one example of a node table 130. FIG. 6B is a table for showing one example of an edge table 135.

The graph structure is a data structure representing a large number of elements (hereinafter referred to as "nodes") and a connection between two elements (hereinafter referred to as "edges") and can express a vicinal relationship between particles. The node table 130 shown in FIG. 6A is a table for showing particles that are nodes, and the edge table 135 shown in FIG. 6B is a table for showing vicinal relationships that are edges. Those two tables are hereinafter sometimes referred to collectively as "graph structure table".

In FIG. 6A and FIG. 6B, as one example, the numbers of the white area groups illustrated in FIG. 1D and vicinal relationships are assigned to elements in each table. In registration of a white area group, first, it is confirmed that the white area group has not been recorded as a row in the node table 130 or the edge table 135. When the white area group has not been recorded, information on the white area group is recorded in a row next to the recorded row. Thus, data having a graph structure on the vicinal particles is obtained in the vicinal particle extraction step S101.

In a particle pair presence/absence determination step S122, the presence or absence of a particle white area that has not been registered in the graph structure table is determined. When the particle white area is present, the flow is returned to the particle pair selection step S120. When the particle white area is not present, the graph structure table is used as output in the vicinal particle extraction step S101.

Figure 7A:
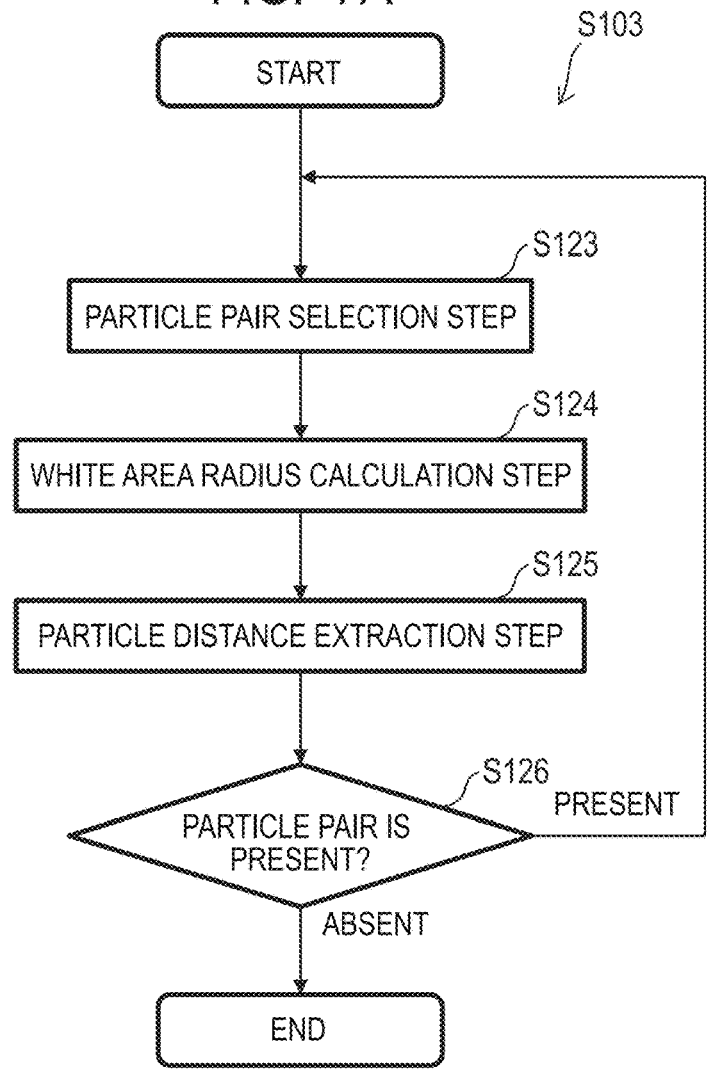
FIG. 7A is a flowchart for illustrating one example of a processing procedure of the vicinal particle extraction step in a case where the white area between the particles cannot be detected.
Figure 7B:
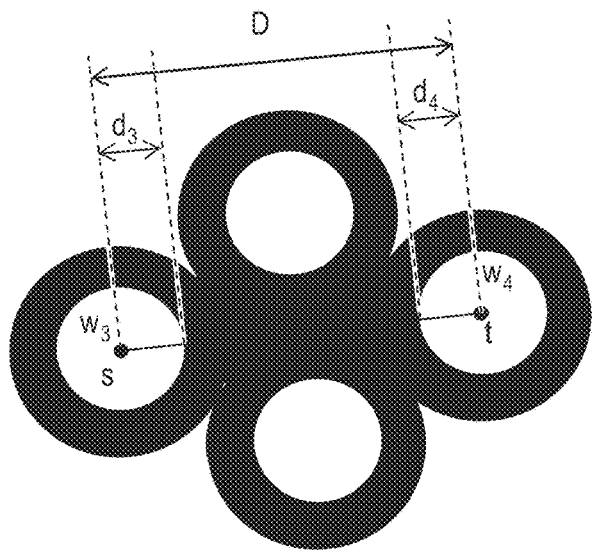
FIG. 7B is a view for illustrating one example of a relationship between the white area and the black area in the binary image in the case where the white area between the particles cannot be detected.

A vicinal particle extraction step S103, which is an example in which the procedure is different from that in the vicinal particle extraction step S101, is described with reference to FIG. 7A and FIG. 7B. FIG. 7A and FIG. 7B are a flowchart and a view, respectively, for illustrating one example in a case where a white area is not present between particles, that is, a white area between particles cannot be detected. FIG. 7A is a flowchart for illustrating one example of a processing procedure of the vicinal particle extraction step S103. FIG. 7B is a view for illustrating one example of a relationship between a white area and a black area in a binary image. When particle image data is acquired through use of an image pickup lens having a large depth of field or when scattered light of a coloring matter is imaged, such a binary image as illustrated in FIG. 7B is obtained.

A particle pair selection step S123 and a particle pair presence/absence determination step S126 in the flowchart illustrated in FIG. 7A are the same as the particle pair selection step S120 and the particle pair presence/absence determination step S122 in a case where a white area is present between particles, which are illustrated in FIG. 5A.

In a white area radius calculation step S124, on a straight line connecting center positions (coordinates corresponding to positional data) of two selected particle white areas, a maximum distance from the center position to a pixel away from the center position (hereinafter referred to as "white area radius") is calculated in a binary area. In FIG. 7B, center positions of particle white areas "$w_3$" and "$w_4$" are "s" and "t", respectively, and white area radii thereof are "$d_3$" and "$d_4$", respectively.

In a particle distance calculation step S125, a distance between the center positions of the two particle white areas is calculated, and the obtained distance is compared to a total of the white area radii obtained in the white area radius calculation step S124. When the distance between the center positions is equal to or less than twice the total of the white area radii, it is determined that the particle white areas are vicinal to each other, although this determination depends on the size of each of white areas. For example, when white areas located on a line connecting the center positions of the two particle white areas belong to only the two particle white areas, and the difference from the distance between the two center positions is less than a half of the distance between the center positions, it is determined that the particle white areas are vicinal to each other. In FIG. 7B, a center-to-center distance D is more than twice a total of the white area radii "$d_3$" and "$d_4$", and hence it can be determined that the particle white areas are not vicinal to each other. The white area groups determined to be vicinal to each other in the particle distance calculation step S125 are registered in tables expressing the graph structures, which are shown in FIG. 6A and FIG. 6B, in the same manner as in the line search step S121 illustrated in FIG. 5A.

<Calculation Step in Particle Measuring Method>

Figure 8:
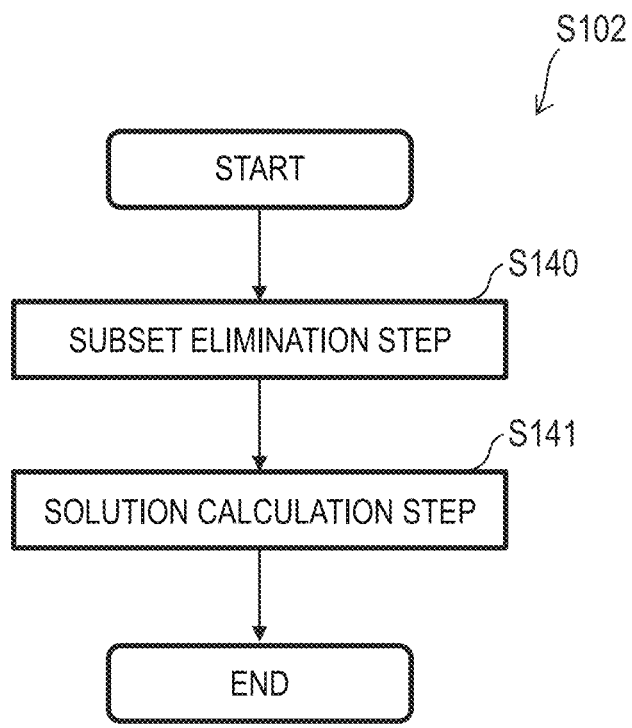
FIG. 8 is a flowchart for illustrating one example of a processing procedure of a calculation step in the particle measuring method according to at least one embodiment of the present invention.

One example of a processing procedure of the calculation step S102 is described with reference to FIG. 8. FIG. 8 is a flowchart for illustrating one example of the processing procedure of the calculation step S102 in the particle measuring method 010 according to at least one embodiment of the present invention.

In a subset elimination step S140, a partial graph structure that is not suitable for calculating a particle radius is eliminated from the node table 130 and the edge table 135, which are output data in the vicinal particle extraction step S101. A particle radius is calculated by a simultaneous equation described later, but a radius can be determined when the simultaneous equation becomes overdetermined. The partial graph structure that is not suitable for calculating a particle radius can be eliminated by excluding a coefficient related to a particle included in a subset from the simultaneous equation when the number of particles is larger than the number of particle pairs. Specifically, among subsets formed of nodes connected to each other, a subset in which the number of edges is smaller than the number of nodes becomes underdetermined, and hence a radius cannot be determined. As a result, this subset is to be eliminated.

Returning to FIG. 6A and FIG. 6B, the extraction of a subset to be eliminated is described. One node number in a column of node numbers is selected from the node table 130 shown in FIG. 6A. When there are nodes having a connection relationship with the selected node, there are rows in which the selected node number is included in small node numbers and large node numbers of the edge table 135 shown in FIG. 6B. The numbers of the nodes having a connection relationship with the selected node can be acquired from those rows. When the processing of searching the rows in the edge table 135 is repeatedly performed with respect to the numbers of the nodes having a connection relationship with the selected node, nodes having a connection relationship with the selected node and edges can be extracted. The number of the nodes and the number of the edges thus obtained are compared to each other. When the number of the edges is smaller than the number of the nodes, the edges and nodes are determined to be eliminated. Regarding the nodes and the edges determined to be eliminated, related rows are removed from the node table 130 and the edge table 135, and the numbers are updated so that the node numbers and the edge numbers are arranged in a sequential order.

In a solution calculation step S141, a simultaneous equation is formed based on the information contained in the node table 130 and the edge table 135 and solved to determine a particle radius.

Examples of the simultaneous equation are described with reference to FIG. 9A to FIG. 9D. FIG. 9A to FIG. 9D are graphs and equations for showing examples of the simultaneous equation to be used for estimating a size of each particle. FIG. 9A is a graph for showing one example of spheres observed from a direction perpendicular to a two-dimensional plane on which the spheres are arranged. FIG. 9B is a graph for showing one example of spheres observed from a direction that is parallel to the plane on which the spheres are arranged and is perpendicular to a plane including a contact point between the spheres and each center of the spheres. FIG. 9C is an equation for showing one example of a simultaneous equation 150 in a case where a particle radius difference is large. FIG. 9D is an equation for showing one example of a simultaneous equation 151 in a case where the particle radius difference can be ignored.

The spheres shown in FIG. 9A and FIG. 9B correspond to spherical particles or particle-including spheres. A relationship between radii "$r_0$" and "$r_1$" and a center-to-center distance "$d_{01}$" of the spheres shown in FIG. 9B can be derived by the Pythagorean theorem as represented by Expression 3 given below.

$$d_{01}^2 + (r_0 - r_1)^2 = (r_0 + r_1)^2 \Leftrightarrow d_{01}^2 = 4r_0 r_1 \Leftrightarrow \log\frac{d_{01}^2}{4} = \log r_0 + \log r_1$$

(Expression 3)

The expression given above is created for each of a plurality of spheres to form the simultaneous equation 150 shown in FIG. 9C. When a difference between radii for each sphere is small, and the influence of a difference in height for each sphere (FIG. 9B) can be ignored, it can be assumed that the center-to-center distance is equal to the sum of the radii. In this case, the simultaneous equation 151 shown in FIG. 9D can also be used.

Next, one example of a procedure for forming the simultaneous equation 150 shown in FIG. 9C from the node table 130 and the edge table 135 shown in FIG. 6A and FIG. 6B to obtain a solution is described. Parameters required for solving the simultaneous equation 150 are a vector (hereinafter referred to as "distance vector") on a left side of the simultaneous equation 150 and a matrix (hereinafter referred to as "adjacent vector") on a right side of the simultaneous equation 150, and those parameters are created first.

The distance vector is a vector having a length equal to the number of the edges. Two node numbers corresponding to the edges are determined by successively following the edge table 135 from the upper row, and particle positions 133 corresponding to the two node numbers are acquired from the node table 130. Elements of the distance vector can be calculated based on the distance between the particle positions 133.

In the adjacent matrix, the numbers of elements in the column and the row correspond to the number of the nodes and the number of the edges, respectively. In creation of the adjacent matrix, two node numbers corresponding to the edges are determined by successively following the edge table 135 from the upper row in the same manner as in the distance vector. Of those, in the row corresponding to the edge number, elements in the column corresponding to the node number are set to 1, and other elements are set to 0. Thus, the adjacent matrix can be created. The adjacent matrix is a sparse matrix in which most of the elements are 0. Therefore, a system involving recording an index of an element having a value of 1 as in a compressed row storage (CRS) system can also be adopted.

After the distance vector and the adjacent matrix are determined, a vector on the right side of the simultaneous equation 150 can be determined by applying a solver of the simultaneous equation. When the number of spheres is more than 10,000, the size of the adjacent matrix becomes larger, and hence a general solver using an LU decomposition cannot be applied. In this case, a solver that can be applied to a large-scale sparse matrix, for example, a least-squares QR (LSQR) method, is used. A radius of each of the spheres can be obtained by calculating an exponential function with elements in the obtained vector on the right side being an exponential term.

As described above, the particle measuring method 010 according to at least one embodiment of the present invention can obtain, based on image data in which it is difficult to measure a contour of each of particles, a size of each of the particles included in the image data.

[Target Nucleic Acid Counting Method]

Now, a target nucleic acid counting method in at least one embodiment of the present invention is described with reference to the drawings.

<Image Data to be Handled by Target Nucleic Acid Counting Method and Object to be Measured>

First, image data to be handled by the target nucleic acid counting method in at least one embodiment is described. Light intensity distribution data (hereinafter referred to as "fluorescence imaging data") on a spectral component related to a target nucleic acid, which is imaged in fluorescence generated when particles are irradiated with excitation light, is used as input data. In the fluorescence imaging data, a pixel value of a particle containing one or more target nucleic acids is larger than a pixel value of a particle free of the target nucleic acid. Therefore, both the pixel values can be distinguished from each other, for example, in threshold processing. In the following description, a particle having a large pixel value in the fluorescence imaging data is referred to as "positive particle", and a particle having a small pixel value is referred to as "negative particle".

An object to be measured by the target nucleic acid counting method in at least one embodiment is the number of target nucleic acids (per reference volume) contained in a solution from which particles are generated. It should be noted that the above-mentioned number of target nucleic acids is different from the number of target nucleic acids amplified after the application of a PCR method or the number of fluorescing positive particles.

<Flow of Entire Target Nucleic Acid Counting Method>

Figure 10:
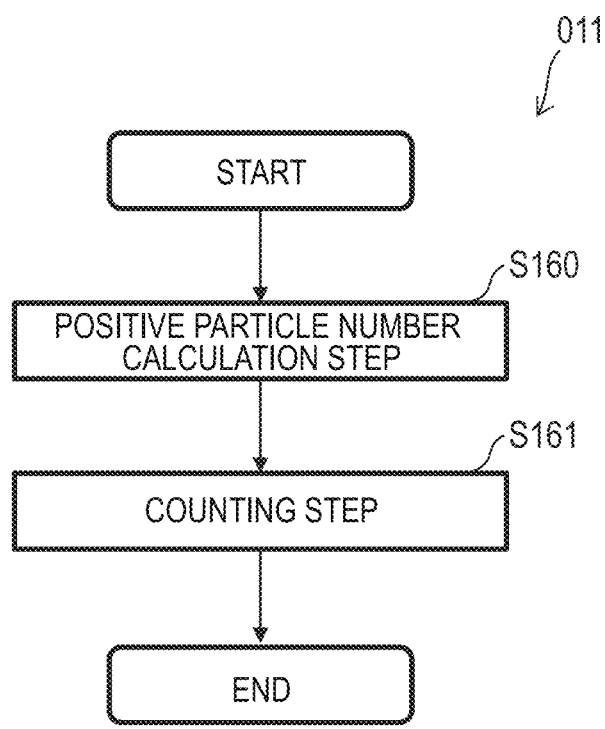
FIG. 10 is a flowchart for illustrating one example of a processing procedure of a target nucleic acid counting method in at least one embodiment of the present invention.

One example of a processing procedure of a target nucleic acid counting method 011 in at least one embodiment of the present invention is described with reference to FIG. 10. FIG. 10 is a flowchart for illustrating one example of the processing procedure of the target nucleic acid counting method 011 in at least one embodiment.

A positive particle number calculation step S160 is a step of extracting positive particles from fluorescence imaging data to calculate the number of positive particles. The positive particles are determined to be extracted by comparing a pixel value at the particle position obtained by the particle measuring method 010 or an average pixel value in an area in the vicinity of the particle position to a threshold value. The threshold value is a value calculated from an amount of statistics of pixel values of the fluorescence imaging data obtained through use of a fluorescence imaging apparatus in a previous experiment.

A counting step S161 is a step of estimating a concentration of target nucleic acids (number of target nucleic acids per unit volume) based on the number of the positive particles obtained in the positive particle number calculation step S160, the particle number and size measured by the particle measuring method 010, and a reference value regarding the particle size.

The reference value is an amount of statistics obtained in the previous experiment, and as the reference value, for example, an average value of sizes of particles or a total volume of measurable particles can be used. In the particle measuring method 010, each size of spheres, which surround the periphery of each particle and are brought into contact with each other, is obtained. However, it is difficult to arrange the particles so that the particles are brought into contact with each other without a gap therebetween. The shape of each of the particles is not a perfect sphere, and hence there is a risk in that the accuracy of a size of each of the particles may be excessively decreased only in the particle measuring method 010. For the foregoing reason, correction using the above-mentioned reference value may be required in some cases.

<Simulation in Comparative Examples>

Before details of the counting step S161 in the target nucleic acid counting method 011 in at least one embodiment of the present invention are described, problems of two target nucleic acid concentration estimating methods, which are generally used, are described as Comparative Examples.

Poisson Distribution Method (Comparative Examples 1 to 3)

In a general dPCR method, a concentration "f" of target nucleic acids is estimated through use of a Poisson distribution method represented by Expression 4 (hereinafter referred to as "Poisson distribution method") given below.

$$f(N_A, N_P, V_a) = -\frac{\log\left(1 - \frac{N_P}{N_A}\right)}{V_a} \quad \text{(Expression 4)}$$

In Expression 4, $N_A$ represents the number of particles, $N_P$ represents the number of positive particles, and $V_a$ represents a volume of each of the particles. It is known that the Poisson distribution method functions normally when the volumes of all the particles are constant, and involves an error when there is a variation in size of the particles.

A simulation that was performed in order to verify the influence of an estimation error of the Poisson distribution method is described. This simulation is performed through use of common parameters in two target nucleic acid estimating methods (a weighted averaging method corresponding to a Comparative Example and the counting step S161 corresponding to an Example) described later, and enables comparison of performance between those procedures. In the simulation, Monte Carlo simulation (hereinafter sometimes referred to as "Monte Carlo method"), which involves distributing target nucleic acids in a concentration determined in advance to particles at a probability that depends on the size of each of the particles, is performed to estimate a concentration based on the number of particles and the number of positive particles obtained by the simulation. The number of positive particles, which is the result of the Monte Carlo simulation, is varied for each trial. Therefore, it is preferred that distribution and estimation be tested out a plurality of times to calculate a concentration average estimate value and a concentration standard deviation. It can be said that, as a difference between the concentration average estimate value and a concentration true value given in advance in the simulation is closer to 0, and the concentration standard deviation is closer to 0, the performance of the target nucleic acid concentration estimating method is higher. As evaluation values of both the procedures, an average value error ratio T (Expression 5 given below) and a 95% confidence interval ratio S (Expression 6 given below) are defined, and can be used for comparison of simulation results.

$$T = \frac{g_{est} - g_{org}}{g_{org}} \times 100 \quad \text{(Expression 5)}$$

In Expression 5, "$g_{est}$" represents a concentration average estimate value, and "$g_{org}$" represents a concentration true value that was given in advance in the simulation.

$$S = \frac{1.96 \times \sigma}{g_{org}} \times 100 \quad \text{(Expression 6)}$$

In Expression 6, "σ" represents a concentration standard deviation.

The parameters that were used in common in the simulation are described. The number of particles is set to 1,500, and regarding the variation in particle, a radius standard deviation of the particles is set to 20% of the radius. The number of times of execution of the distribution and estimation is set to 50. The simulation for verifying accuracy was performed by changing a ratio (hereinafter referred to as "positive ratio") of the number of positive particles to the number of particles. In FIG. 11, results of the simulation are shown.

FIG. 11 is a table for showing the results of the simulation for verifying estimation accuracy of the Poisson distribution method and the weighted averaging method as the Comparative Examples. There was obtained each numerical value of a concentration target value (copies/ul), an average estimate value (copies/ul), a standard deviation (copies/ul), an average value error ratio (%), and a 95% confidence interval ratio (%), at a time when the value of the positive ratio (%) corresponding to the concentration target value was changed to 1%, 10%, and 50% in each of the concentration estimating methods. The detail of the weighted averaging method is described later.

As shown in FIG. 11, in the Poisson distribution method, when the positive ratio is 1% and 10%, the average value error ratio with respect to a target value that is a true target nucleic acid concentration is less than 1% and about 2%, respectively, and hence those average value error ratios fall within an allowable range. However, when the positive ratio is 50%, the average value error ratio becomes about 10%, which exceeds the allowable range.

A measurement error in the related art using the dPCR method is suppressed to ±10% or less of a true value in the 95% confidence interval. However, when the Poisson distribution method is used, a 10% error occurs only with the average value error ratio, which is a value free of the measurement error. Therefore, it is difficult to apply the Poisson distribution method to the particles having a variation in size instead of the counting step S161.

Weighted Averaging Method (Comparative Examples 4 to 6)

Next, the weighted averaging method is described. The weighted averaging method is a target nucleic acid concentration estimating procedure that is generally used, and is a procedure involving grouping particles having substantially the same size and applying the Poisson distribution method for each group. A concentration estimate value of the weighted averaging method is given by Expression 7 below.

$$f(N_A^{(0)}, N_P^{(0)}, V_a^{(0)}, \ldots, N_A^{(M-1)}, N_P^{(M-1)}, V_a^{(M-1)})$$ (Expression 7)

$$= \sum_{i=0}^{M-1} -\frac{w^{(i)} \log\left(1 - \frac{N_P^{(i)}}{N_A^{(i)}}\right)}{V_a^{(i)}}, \text{ where } w^{(i)}$$

$$= \frac{N_A^{(i)} V_a^{(i)}}{\sum_{k=0}^{M-1} N_A^{(k)} V_a^{(k)}}$$

In Expression 7, $N_A^{(i)}$, $N_P^{(i)}$, and $V_a^{(i)}$ (i=0, 1, ..., M−1) represent the number of particles, the number of positive particles, and an average volume of the particles, respectively, in a group No. "i" in M groups. "$w^{(i)}$" represents a weight to be multiplied by a concentration obtained from each of the groups, and is a value obtained by dividing a particle volume total value in the group No. "i" by a total volume value of all the particles.

The problem of the weighted averaging method lies in that, as the number of groups is increased, the number of particles belonging to each of the groups is decreased. When the number of particles is decreased, the values of the positive ratios ($N_P^{(i)}/N_A^{(i)}$) obtained for each group in Expression 7 do not become continuous, and estimation accuracy is decreased due to the influence of a quantization error. Target nucleic acid estimate values having low accuracy determined for each group are summed up, and the estimation accuracy of an average concentration is also decreased.

The results of a simulation that was performed in order to verify the degree of an estimation error of the weighted averaging method are described with reference to FIG. 11. As shown in FIG. 11, in the weighted averaging method (Comparative Examples 4 to 6), the average value error ratio is suppressed to 4% or less irrespective of the positive ratio. However, the 95% confidence interval ratio is a value of 8% or more in any of Comparative Examples 4 to 6, and is a significantly large numerical value of 42.9% at the positive ratio of 1%. In the weighted averaging method, for example, the influence of an error in the 95% confidence interval ratio can be suppressed by increasing the number of particles. However, when the number of particles is as small as 1,500, the accuracy is decreased, and hence it is difficult to apply the weighted averaging method instead of the counting step S161.

<Counting Step in Target Nucleic Acid Counting Method>

Now, the counting step S161 in the target nucleic acid counting method 011 in at least one embodiment of the present invention is described in detail.

Figure 12:
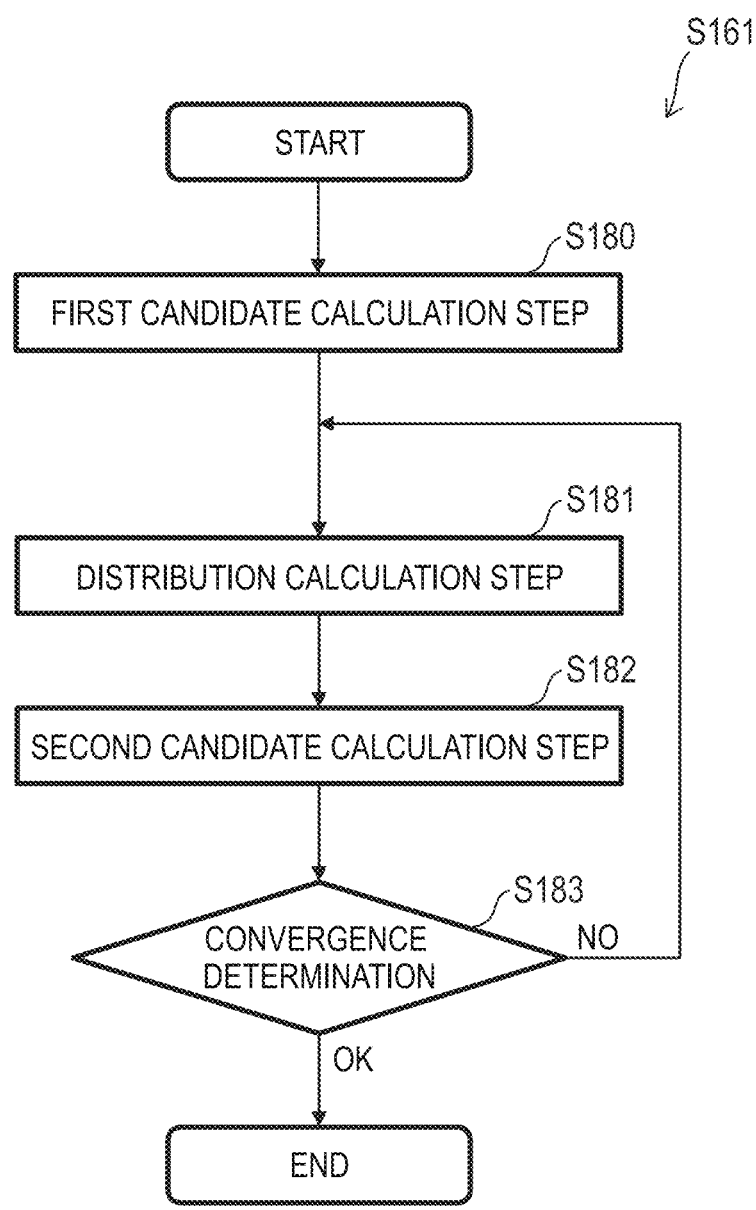
FIG. 12 is a flowchart for illustrating one example of a processing procedure of a counting step in the target nucleic acid counting method in at least one embodiment of the present invention.

The concentration estimating method to be performed in the counting step S161 is a procedure that has been newly developed so as to solve the problem of a decrease in accuracy occurring in the Poisson distribution method and the weighted averaging method. One example of a processing procedure of the counting step S161 is described with reference to FIG. 12. FIG. 12 is a flowchart for illustrating one example of a processing procedure of the counting step S161 in the target nucleic acid counting method 011 in at least one embodiment of the present invention.

A first candidate calculation step S180 is a step of calculating a first candidate value of a concentration through use of Expression 4 based on the number of positive particles, the number of particles, the size of each of the particles, and the reference value of the size. As the volume $V_a$ of each of the particles required in Expression 4, the size of each of the particles or the average particle volume calculated through use of the reference value is used.

A distribution calculation step S181 is a step of performing the Monte Carlo simulation of distributing, to each of the particles, the target nucleic acids calculated based on a second candidate value of a concentration. The number of positive particles is calculated based on the distribution of the target nucleic acids obtained by the Monte Carlo simulation. When the second candidate value of a concentration has not been determined, any positive integer can be adopted as an initial value. When a numerical value distant from a true concentration is adopted as the initial value, convergence is delayed. Therefore, it is preferred that the first candidate value or the number of positive particles obtained in the positive particle number calculation step S160 be set to the initial value. The details of the Monte Carlo simulation are described later.

A second candidate calculation step S182 is a step of calculating an update value of the second candidate through use of the number of positive particles obtained in the distribution calculation step S181. The update value is given by Expression 8 below.

$$g_{i+1} = g_i - f(N_A, N_P', V_a) + f_0$$ (Expression 8)

In Expression 8, "$g_i$" represents the second candidate value used in the distribution calculation step S181, and "$g_{i+1}$" represents the update value of the second candidate value. "f", "$N_A$", and "$V_a$" are the same as those in Expression 4, but "$N_P'$" represents the number of positive particles obtained in the distribution calculation step S181. "$f_0$" represents the first candidate value.

A convergence determination step S183 includes determining whether or not an absolute value of a difference between the second candidate value used in the distribution calculation step S181 and the update value obtained in the second candidate calculation step S182 is less than an allowable value. The update value is varied in the Monte Carlo simulation, and hence it is difficult to adopt an excessively small allowable value. In general, it is preferred that a value of about 0.1% of the first candidate value be adopted.

When it is determined by the convergence determination step S183 that the absolute value is equal to or more than the allowable value, the distribution calculation step S181, the second candidate calculation step S182, and the convergence determination step S183 are repeated through use of the update value as the second candidate value. When it is determined by the convergence determination step S183 that the absolute value is less than the allowable value or when the repetition number is equal to or more than a predetermined number, the second candidate value is set as a concentration estimate value. The convergence property and accuracy in the counting step S161 are described later. In the counting step S161, higher accuracy is obtained without being influenced by the target nucleic acid concentration or the number of particles as compared to the Poisson distribution method and the weighed averaging method.

<Monte Carlo Simulation>

Figure 13:
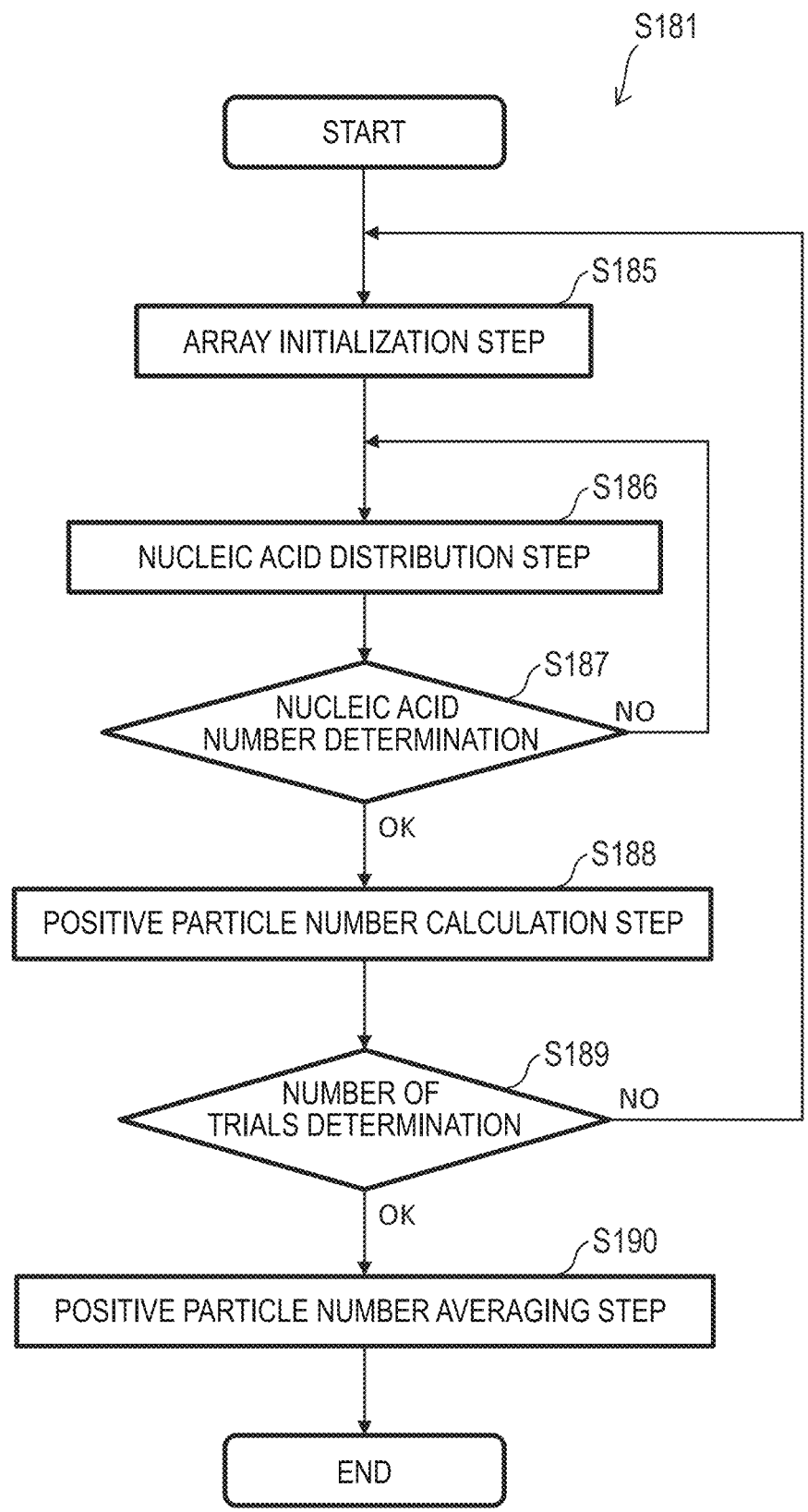
FIG. 13 is a flowchart for illustrating one example of a processing procedure of Monte Carlo simulation in a distribution calculation step included in the counting step.

A processing procedure of the Monte Carlo simulation to be performed in the distribution calculation step S181 in the counting step S161 is described with reference to FIG. 13. FIG. 13 is a flowchart for illustrating one example of the processing procedure of the Monte Carlo simulation in the distribution calculation step S181 included in the counting step S161.

An array initialization step S185 is a step of preparing an integer array (hereinafter referred to as "nucleic acid holding array") for holding the number of nucleic acids distributed to each of particles and initializing a value of an array element to 0. In the following, a method involving assigning a number (hereinafter referred to as "particle number") of from 0 to ("number of particles"-1) to each of the particles and associating the element numbers in the nucleic acid holding array with the particle numbers is described. Each numerical value in the nucleic acid holding array in this method represents the number of nucleic acids contained in a particle of the particle number that is the same as the number of the array element.

A nucleic acid distribution step S186 is a step of selecting a particle number (element number in the nucleic acid holding array) in accordance with the probability related to the size of each of the particles and adding 1 to a numerical value of the nucleic acid holding array element. In selection of the particle number, an equation regarding a probability function P(q) given by Expression 9 below is solved to determine a particle number "q" corresponding to a uniform random number "s" having a value of from 0 to 1.

$$s = P(q) = \sum_{i=0}^{q} T_i \qquad \text{(Expression 9)}$$

In Expression 9, "$T_i$" represents a ratio determined based on the size of a particle of the particle number "i" and is a value obtained by dividing the volume of a spherical particle (or a particle-including sphere) by a total volume equivalent value. The total volume equivalent value is a value equivalent to a total volume of all the spherical particles (or all the particle-including spheres). When the measurement accuracy of a volume of each of the spherical particles (or each of the particle-including spheres) is low, there is a risk in that a total value may be significantly deviated from a correct value. In this case, the total volume equivalent value may be determined through use of the above-mentioned reference value. When the reference value is an average volume of the particles, which is statistically determined, a value obtained by multiplying the reference value by the number of particles can be adopted as the total volume equivalent value. When the reference value is, for example, a solution amount before generation of the particles, a value obtained by subtracting a loss at a time of generation of the particles from the reference value can be adopted as the total volume equivalent value.

The probability function P(q) returns a discrete value, and hence the equation cannot be solved through use of the random number "s", which is a continuous value, with the result that it is required to determine an approximate solution. For example, the particle number "q" given by Expression 10 below can be used as the approximate solution.

$$q_a = \underset{a}{\mathrm{argmin}}(W(P(q)-s)),\ W(x) = \begin{cases} x & \text{if } x \geq 0 \\ 1 & \text{if } x < 0 \end{cases} \qquad \text{(Expression 10)}$$

Although approximation accuracy is decreased, the approximate solution can also be determined at a high speed by creating a look-up table (hereinafter abbreviated as "LUT"). For example, when the LUT is created through use of a numerical value array having a sufficiently large number "N" of elements, a value of an element from an element number "$p_s$" to an element number "$p_l$" given by Expression 11 below is set to the particle number "q".

$$p_s = \begin{cases} \mathrm{floor}(N \times P(q-1)) & \text{if } q \geq 1 \\ 0 & \text{if } q = 0 \end{cases}, \qquad \text{(Expression 11)}$$

$$p_l = \mathrm{floor}(N \times P(q)) - 1$$

In Expression 11, floor(x) represents a function of dropping the fractional portion of a floating-point number "x". Elements in the LUT can be set to particle numbers by generating element numbers of from 0 to N−1 through use of the uniform random number "s".

In a nucleic acid number determination step S187, the number of times of execution of the nucleic acid distribution step S186 is compared to the second candidate value. The nucleic acid distribution step S186 is repeated until the number of times of execution of the nucleic acid distribution step S186 becomes equal to the second candidate value.

A positive particle number calculation step S188 is a step of calculating the number of positive particles based on the nucleic acid holding array.

In a number-of-trials determination step S189, the number of times of execution from the array initialization step S185 to the positive particle number calculation step S188 is compared to the number of trials determined in advance. Through use of the random number in the nucleic acid distribution step S186, the number of positive particles varied for each trial is obtained.

A positive particle number averaging step S190 is a step of determining an average value of the number of positive particles obtained for each trial. A positive particle number average value having a small variation can be obtained by performing a sufficient number of trials.

In the above description, a method involving associating the element numbers in the nucleic acid holding array with the particle numbers has been described. However, another implementation method may be used. For example, it is also possible to adopt a method involving assuming minute sections sufficiently smaller than the particles and associating the element numbers in the nucleic acid holding array with numbers of the minute sections. In this case, a set of a plurality of minute sections corresponds to one particle. The nucleic acid distribution step S186 is set to a step of selecting the numbers of the minute sections in accordance with a uniform probability instead of the probability related to the size of each of the particles and adding 1 to values of the elements in the nucleic acid holding array. A total of the element values of the minute sections corresponding to one particle represents the number of nucleic acids contained in the particle.

<Convergence Property and Effect of Counting Step>

The convergence property of iterative processing to be performed in the counting step S161 can be described through use of Banach fixed-point theorem (theorem of contractive mapping). The Banach fixed-point theorem shows that, in a function g(x) satisfying Expression 12 given below, there is a fixed point $x_f=g(x_f)$, and the fixed point $x_f$ is obtained by performing iterative processing $x_{i+1}=g(x_i)$ (i=0, 1, 2, ... ).

$$|g(a)-g(b)| \le |a-b| \quad \text{(Expression 12)}$$

In Expression 12, "a" and "b" represent any two points located in a section in which the iterative processing is performed.

When the second candidate value, which is an input value in the distribution calculation step S181, is represented by "x", and the function of continuously performing the distribution calculation step S181 and the second candidate calculation step S182 is represented by "g", the expression can be developed as in Expression 13 given below.

$$g(x)=h \circ H(x), h(y)=H^{-1}(y)-f(N_A, y, V_a)+f_0 \quad \text{(Expression 13)}$$

In Expression 13, H(x) represents a function of calculating the number "y" of positive particles based on the second candidate value "x" in the distribution calculation step S181, and h(y) represents a function of calculating an update value of the second candidate value "x" based on the number "y" of positive particles in the second candidate calculation step S182. $H^{-1}(y)$ represents a virtual inverse function of H(x), which is the distribution calculation step S181. It may be considered that an algorithm in the counting step S161 includes adjusting the second candidate value "x" so that h(y) becomes $H^{-1}(y)$, that is, the number "y" of positive particles matches the number of positive particles obtained by measurement. "f", $N_A$, and $V_a$ are the same as those in Expression 4, and "$f_0$" represents the first candidate value.

Meanwhile, an ideal concentration estimation equation $H^{-1}(y)$ can be approximated by a function represented by Expression 14 given below, in which an error that depends on the number of positive particles is subtracted from Expression 4, which is the Poisson distribution method.

$$H^{-1}(y) \approx f(N_A, y, V_a) - D(y) + R(y) \quad \text{(Expression 14)}$$

In Expression 14, D(y) represents a function representing an error that occurs in the Poisson distribution method. R(y) represents the influence (fluctuation in concentration estimate value) of a variation in number of positive particles, which occurs in the Monte Carlo simulation performed in the function H(y). In the table shown in FIG. 11, D(y) corresponds to a difference between an average estimate value and a target value, and R(y) corresponds to a standard deviation.

When Expression 14 is substituted into Expression 13, $f(N_A, y, V_a)$ is offset, and the expression can be converted into an expression of only an error and a constant as in Expression 15 given below.

$$g(x) = -D \circ H(x) + R \circ H(x) + f_0 = -D_h(x) + R_h(x) + f_0 \quad \text{(Expression 15)}$$

In Expression 15, a composite function of H(x) and D(y) is represented by $D_h(x)$, and a composite function of R(x) and D(y) is represented by $R_h(x)$.

Expression 15 satisfies Expression 12, which is the condition of the Banach fixed-point theorem as described below. When Expression 15 is substituted into Expression 12, a relational expression represented by Expression 16 given below is obtained.

$$|-D_h(a)+R_h(a)+D_h(b)-R_h(b)| \le |a-b| \quad \text{(Expression 16)}$$

When there is a difference between values of two points "a" and "b", the value of the larger point (it is assumed that the point "a" is larger) becomes dominant on the right side of Expression 12. In rows regarding the Poisson distribution method in the table shown in FIG. 11 (that is, Comparative Examples 1 to 3), $D_h(x)$ corresponds to a difference between an average estimate value and a target value, and $R_h(x)$ corresponds to a standard deviation. Therefore, $D_h(a)$ becomes dominant on the left side of Expression 12. When an error ratio of the average estimate value in FIG. 11 is focused, the size of $D_h(a)$ is set to a value of 10.6% or less of the point "a", and Expression 15 satisfies the condition of Expression 12.

Meanwhile, when the values of the two points "a" and "b" are substantially the same, $D_h(x)$ does not change drastically in response to a minute change of "x", and hence $D_h(a)-D_h(b)$ becomes about 0. As a result, Expression 15 can satisfy the condition of Expression 12 by decreasing $R_h(a)-R_h(b)$, which is a variation in value in the Monte Carlo simulation. The variation in value in the Monte Carlo simulation can be suppressed by increasing the number of trials in the number-of-trials determination step S189 described with reference to FIG. 13. Specifically, the accuracy can be improved by increasing the number of trials in the number-of-trials determination step S189 as the convergence of the iterative processing performed in the counting step S161 proceeds.

From the foregoing, when the iterative processing is applied to the function g(x) of continuously performing the distribution calculation step S181 and the second candidate calculation step S182, the fixed point $x_f=g(x_f)$ can be determined. The obtained fixed point "$x_f$" represents a concentration estimate value at a time when the number of positive particles obtained by the Monte Carlo simulation matches the number of positive particles obtained by measurement.

Results of simulation, in which the estimation accuracy of the counting step S161 is actually verified, are described with reference to FIG. 14. FIG. 14 is a table for showing one example of results obtained by verifying estimation accuracy of the counting step S161 in the target nucleic acid counting method 011 in at least one embodiment of the present invention. The details of the simulation are the same as those of the simulation of the Poisson distribution method and the weighted averaging method shown in FIG. 11. As Examples 1 to 3, there was obtained each numerical value of a concentration target value (copies/ul), an average estimate value (copies/ul), a standard deviation (copies/ul), an average value error ratio (%), and a 95% confidence interval ratio (%), at a time when the value of the positive ratio (%) corresponding to the concentration target value was changed to 1%, 10%, and 50%.

As shown in FIG. 14, the average value error ratio is suppressed to 1% or less irrespective of the positive ratio, and the 95% confidence interval ratio is also suppressed to 7% or less. Thus, through use of the target nucleic acid counting method 011 in at least one embodiment of the present invention, a target nucleic acid concentration can be obtained with high accuracy even when the number of particles is small.

[Concentration Measuring System and Apparatus, and Particle Measuring Apparatus]

Now, a concentration measuring system and apparatus, and a particle measuring apparatus according to at least one embodiment of the present invention, which include software having implemented the particle measuring method or the target nucleic acid counting method in at least one embodiment of the present invention, are described. However, the present invention is not limited thereto. The concentration measuring system and apparatus, and the particle measuring apparatus according to least one embodiment of the present invention achieve measurement of, based on image data on a specimen including a plurality of particles, a size of each of the particles included in the image data.

First Embodiment

Figure 15:
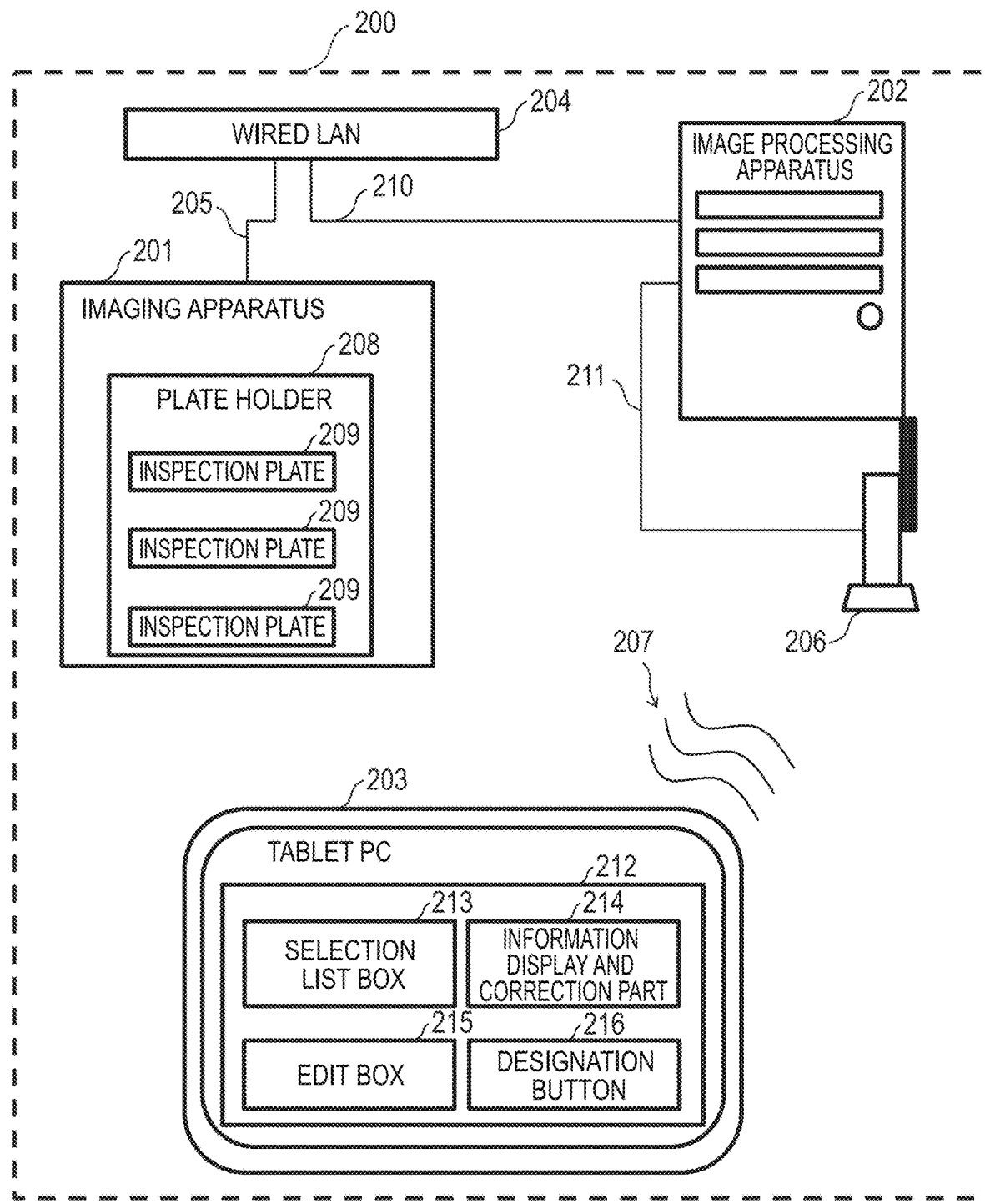
FIG. 15 is a diagram for illustrating one example of a configuration of a concentration measuring system according to a first embodiment of the present invention.

A concentration measuring system according to a first embodiment of the present invention is described with reference to FIG. 15. FIG. 15 is a diagram for illustrating one example of a configuration of a concentration measuring system 200 according to the first embodiment. As illustrated in FIG. 15, the concentration measuring system 200 according to the first embodiment includes an imaging apparatus 201, an image processing apparatus 202, a tablet PC 203, a wired LAN 204, and a wireless LAN router 206.

The imaging apparatus 201 is connected to the wired LAN 204 through, for example, a network cable 205 such as an Ethernet (trademark) cable. The imaging apparatus 201 includes a plate holder 208, and a plurality of inspection plates 209 can be set on the plate holder 208. The detailed configuration of the imaging apparatus 201 is described later.

The image processing apparatus 202 is connected to the wired LAN 204 through a network cable 210. In addition, the image processing apparatus 202 is connected to the wireless LAN router 206 through a network cable 211. The image processing apparatus 202 can communicate to/from the tablet PC 203 via radio communication 207 through the wireless LAN router 206.

The tablet PC 203 can communicate to/from the image processing apparatus 202 via the radio communication 207 through the wireless LAN router 206. The tablet PC 203 includes a display screen 212 configured to display a state of the imaging apparatus 201. On the display screen 212, a selection list box 213, an information display and correction part 214, an edit box 215, and a designation button 216 can be displayed.

<Flow of Processing in Concentration Measuring System>

Next, a flow of processing to be performed in the concentration measuring system 200 is described. First, a user of the concentration measuring system 200 sets the inspection plates 209 on the plate holder 208 of the imaging apparatus 201. The details of the inspection plates 209 are described later. The imaging apparatus 201 sends information (slot numbers in the plate holder 208 and barcode information on the inspection plates 209) on the inspection plates 209, which have been set to the image processing apparatus 202. After that, the imaging apparatus 201 shifts to a standby mode, in which the imaging apparatus 201 inquires of the image processing apparatus 202 for work designation at fixed intervals. The image processing apparatus 202 also has a Web server function, and is configured to display information (for example, identification information decoded from the barcode information on the inspection plates 209 and a measuring method) on the available imaging apparatus to the user.

Next, the user of the concentration measuring system 200 logs in to a Web site displayed to the user by the image processing apparatus 202 through use of the tablet PC 203, thereby being able to open the display screen 212 configured to display the state of the imaging apparatus 201. After the imaging apparatus 201 is selected by the selection list box 201 through operation of the user, the tablet PC 203 displays the identification information on the inspection plates 209, the measuring method, and a predicted value of a measurement time in the information display and correction part 214. When the barcodes are not attached to the inspection plates 209, default values of the identification information and the measuring method are displayed, and hence the default values are corrected on the screen through operation. After the identification information (for example, a measurement date and a label) of the measurement results is input to the edit box 215 for input through operation, the designation button 216 configured to designate the start and end of imaging is clicked on. Then, the tablet PC 203 sends the input and corrected information and the designation of imaging to the image processing apparatus 202.

After the imaging apparatus 201 confirms the designation of imaging from the image processing apparatus 202, the imaging apparatus 201 is shifted from the standby mode to an imaging mode. The configuration of the imaging apparatus 201 and the operation thereof at a time of the imaging mode are described later. The imaging apparatus 201 sends particle image data and fluorescence imaging data on the inspection plates 209 to the image processing apparatus 202 while performing imaging. After the completion of imaging and sending of the entire image data, the imaging apparatus 201 is shifted to the standby mode.

The image processing apparatus 202 executes the software having implemented the particle measuring method 010 illustrated in FIG. 2 on the particle image data sent from the imaging apparatus 201, and calculates a position and a size of each of the particles. Then, the image processing apparatus 202 executes the software having implemented the target nucleic acid counting method 011 illustrated in FIG. 10 on the fluorescence imaging data sent from the imaging apparatus 201 and the position and size of each of the particles, to thereby calculate a concentration. In the above-mentioned software, a reference value of the size of each of the particles is not used. The image processing apparatus 202 displays the calculated concentration value to the user on the Web site.

The user of the concentration measuring system 200 logs in to the Web site displayed to the user by the image processing apparatus 202 through use of the tablet PC 203, thereby being able to confirm the measured concentration value, which is newly displayed in the information display and correction part 214.

<Inspection Plate>

Figure 16A:
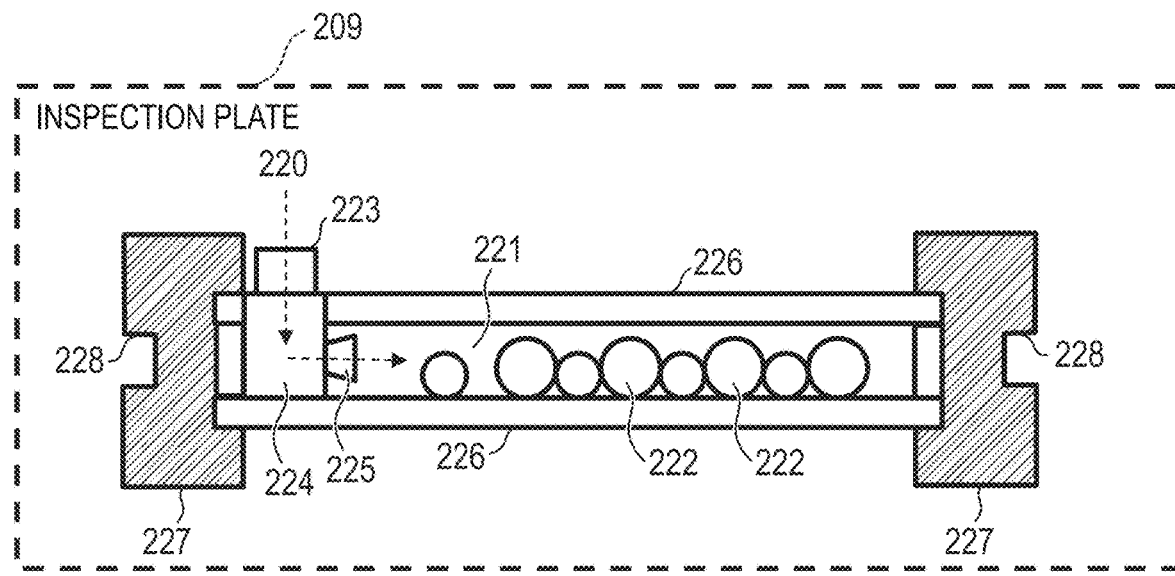
FIG. 16A is a sectional view of an inspection plate for illustrating one example of the structure of the inspection plate configured to hold particles in the concentration measuring system according to the first embodiment.
Figure 16B:
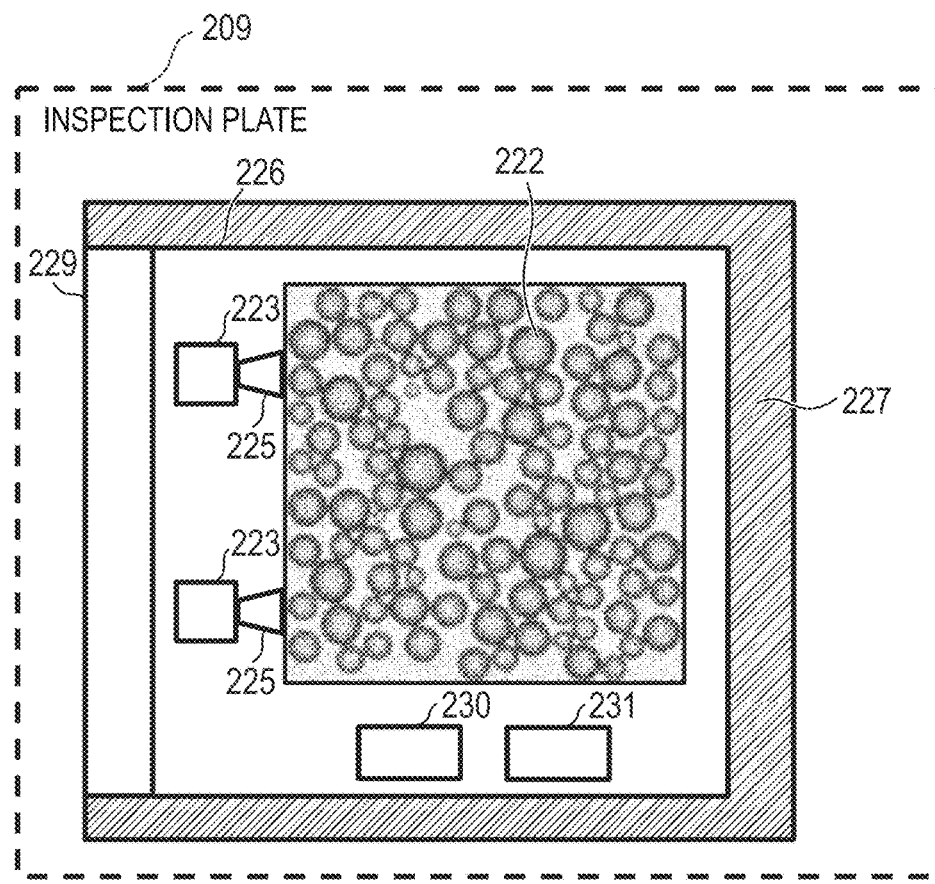
FIG. 16B is a plan view of the inspection plate illustrated in FIG. 16A.

The structure of the inspection plate 209 is described with reference to FIG. 16A and FIG. 16B. FIG. 16A and FIG. 16B are each a view for illustrating one example of the structure of the inspection plate 209 configured to hold the particles in the concentration measuring system 200 according to the first embodiment. FIG. 16A is a sectional view of the inspection plate 209. FIG. 16B is a plan view of the inspection plate 209. The inspection plate 209 is an instrument configured to hold a specimen, for example, an instrument capable of holding a solution 220 containing a mixture of target nucleic acids and a reagent (chemical agent containing chemical substances required for performing the PCR method, such as a primer and a fluorescent labeling probe) as a plurality of particles 222 in oil 221.

Next, a method of generating the particles 222 is described. As illustrated in FIG. 16A, first, the oil 221 is injected into a solution injection part 223 with a syringe or the like, and air is sucked out from an oil suction part 225 to fill the oil 221 into the inspection plate 209. The solution 220 is injected into the solution injection part 223 under a state of being pressurized with a syringe or the like, and a large number of particles 222 are generated through a porous film formed in a particle generation part 224. In the first embodiment, the porous film is used for generating the particles 222, but a microchannel tip or the like may be used. The particles 222 each have a specific gravity larger than that of the oil 221, and hence the particles 222 are arranged so as not overlap with one another on a glass substrate 226 of a lower surface.

The particles 222 are easily destroyed due to deformation or the like of the glass substrate 226. Therefore, it is preferred that the periphery of the inspection plate 209 be reinforced with a metal jig 227. When the inspection plate 209 is conveyed by a robot, a claw of a robot hand is brought into contact with a recess 228 of the metal jig 227 so that a force is prevented from being applied to the glass substrate 226. In order to prevent mixing of target nucleic acids (DNAs), the inspection plate 209 cannot be reused, but the metal jig 227 can be reused by being separated through removal of a fastener 229.

A barcode 230 obtained by encoding an identifier of the solution 220 and the measuring method can be attached to the inspection plate 209. The barcode 230 is imaged by the imaging apparatus 201 illustrated in FIG. 15, and the information is decoded in the image processing apparatus 202. The information of the barcode 230 cannot be identified by a human, and hence a label 231, which can be identified by a human, may also be attached to the inspection plate 209.

<Configuration of Imaging Apparatus and Imaging Processing>

Figure 17:
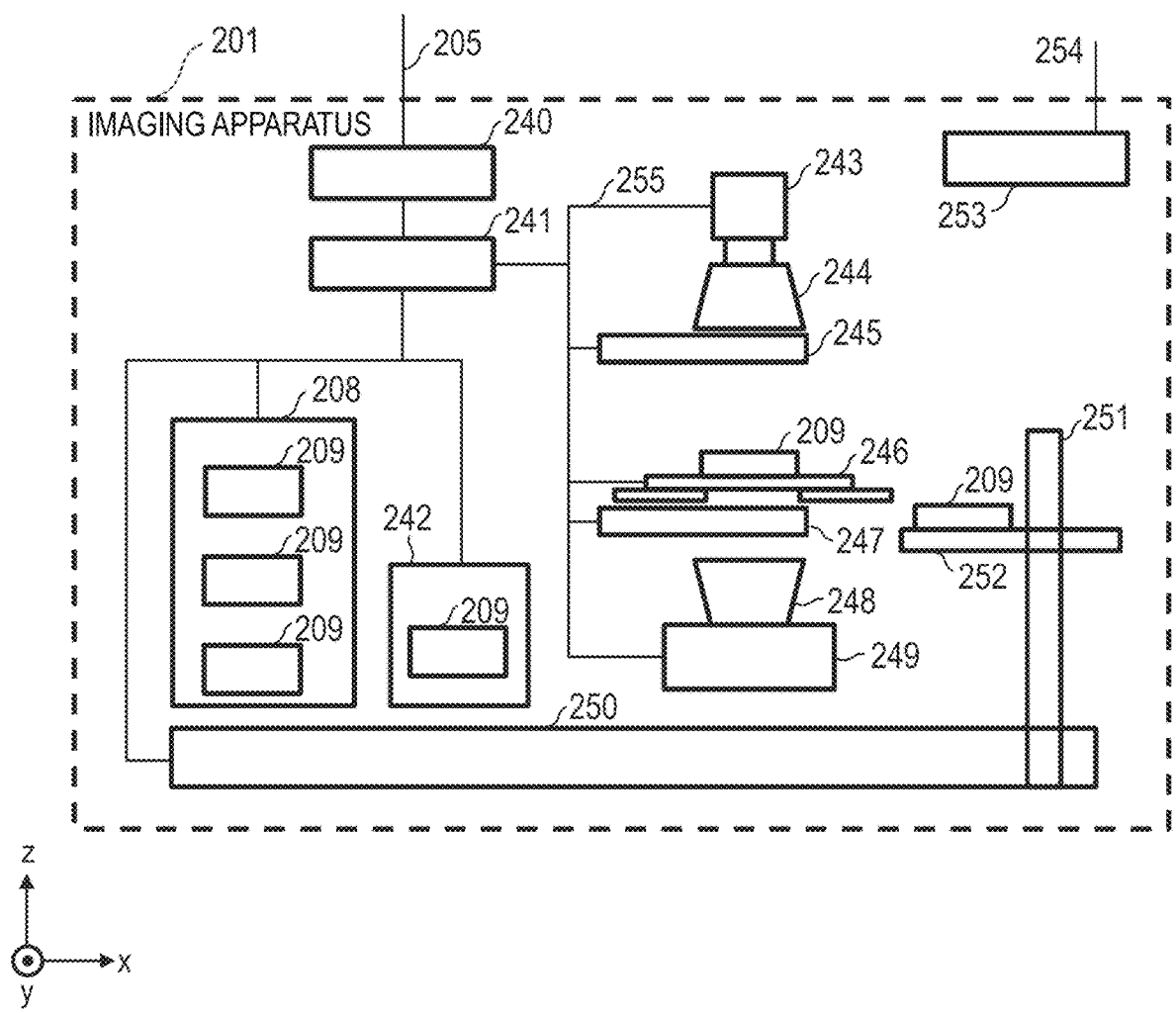
FIG. 17 is a diagram for illustrating one example of a configuration of an imaging apparatus configured to perform a PCR method and fluorescence imaging in the concentration measuring system according to the first embodiment.

The configuration of the imaging apparatus 201 illustrated in FIG. 15 is described with reference to FIG. 17. FIG. 17 is a diagram for illustrating one example of the configuration of the imaging apparatus 201 configured to perform the PCR method and fluorescence imaging in the concentration measuring system 200 according to the first embodiment. As illustrated in FIG. 17, the imaging apparatus 201 includes the plate holder 208, a network interface 240, a controller 241, a thermal cycler 242, a camera 243, an imaging lens 244, a camera-side filter wheel 245, an xy stage 246, an illumination-side filter wheel 247, an illumination optical system 248, an LED light source 249, a single axis robot (x-axis direction drive) 250, a single axis robot (z-axis direction drive) 251, a single axis robot (y-axis direction drive) 252, and a power supply 253. Each constituent element is connected to a network through the network cable 255 and the like.

Next, the operation immediately after the inspection plates 209 are set on the plate holder 208 is described. The controller 241 confirms the positions of slots, in which the inspection plates 209 are inserted, with a sensor in the plate holder 208. Then, the controller 241 drives the single axis robots 250 to 252 to convey each of the inspection plates 209 inserted in the slots onto the xy stage 246 and images the barcode 230. After imaging the barcodes 230 of all the inspection plates 209, the controller 241 sends the numbers of the slots in which the inspection plates 209 are set and the barcode images thereof to the image processing apparatus 202, and is shifted to the standby mode.

Next, the operation to be performed after the shift to the imaging mode is described. The controller 241 acquires information input and corrected by the tablet PC 203 from the image processing apparatus 202. Then, the controller 241 generates a work sequence based on the information acquired from the image processing apparatus 202, and the information on the inspection plates 209, which has already been acquired. The work sequence corresponds to data describing instructions to be issued to the single axis robots 250 to 252 and the camera 243 and timing to issue the instructions. The timing to issue the instructions is determined so as to minimize a waiting time caused by the difference in execution time among components of the imaging apparatus 201 and the difference in measuring method for each of the inspection plates 209. An instruction to send the image data by the network interface 240, as well as the imaging and drive instructions, are included in the work sequence.

As an easy-to-understand example, a simple work sequence, in which one inspection plate 209 is used and fluorescence imaging is performed once, is described. The single axis robots 250 to 252 convey the inspection plate 209 from the plate holder 208 to the thermal cycler 242. A distal end of the single axis robot 252 has a claw (not shown) like a fork of a forklift. The single axis robot 252 can convey the inspection plate 209 without giving vibration thereto by inserting the claw of the single axis robot 252 into the recess 228 formed in the metal jig 227 and lifting the metal jig 227 slightly upward to remove or insert the inspection plate 209. Next, the controller 241 sends an instruction to control a heating temperature and a cooling temperature of a Peltier device to the thermal cycler 242 to perform the PCR method. As the heating temperature and the cooling temperature, values in a table created before shipping are used. Thus, the particle containing the target nucleic acids can be easily detected and measured by amplifying the number of the target nucleic acids in the particle with the PCR method and increasing the intensity of fluorescent emission.

After performing the PCR method, the imaging apparatus 201 conveys the inspection plate 209 onto the xy stage 246 with the single axis robot 252 and starts imaging of particle image data. The controller 241 sends a control instruction to the camera-side filter wheel 245 so that the camera-side filter wheel 245 selects a slot in which an interference filter is not inserted. Further, the controller 241 sends a control instruction to the illumination-side filter wheel 247 so that the illumination-side filter wheel 247 selects an ND filter. In this case, excitation light is not suitable for direct observation due to an excessively high light intensity thereof, and hence it is preferred that the light be reduced with the ND filter. After setting of the camera-side filter wheel 245 and the illumination-side filter wheel 247, the controller 241 sends an instruction for releasing a shutter to the LED light source 249 and an instruction for adjusting an exposure time and imaging to the camera 243. The controller 241 acquires the particle image data from a memory of the camera 243 at a timing when the imaging is completed and data is stored, and sends the data to the image processing apparatus 202 through the network interface 240.

Next, the imaging apparatus 201 performs imaging of fluorescence imaging data. The controller 241 sends a control instruction to the camera-side filter wheel 245 so that the camera-side filter wheel 245 selects a slot of an interference filter for excitation light removal. In addition, the controller 241 sends a control instruction to the illumination-side filter wheel 247 so that the illumination-side filter wheel 247 selects a slot of an interference filter for excitation light transmission. After setting of the camera-side filter wheel 245 and the illumination-side filter wheel 247, the flow is the same as that in the case of the particle image data, although the numerical value of the exposure time is different.

After the controller 241 finishes sending the instructions and sending the image data in accordance with the work sequence, the imaging apparatus 201 is shifted to the standby mode.

The imaging apparatus 201 includes the thermal cycler 242 therein, but the thermal cycler may be another external device. For example, when the inspection plate 209, in which the number of nucleic acids is increased by an external thermal cycler device (not shown), is inserted into the plate holder 208, the imaging apparatus 201 may be configured only to perform imaging.

As described above, the first embodiment of the present invention relates to a target nucleic acid concentration measuring system, which achieves correction of a variation in particle even when it is difficult to acquire a particle volume by imaging, for example, due to the influence of a depth of field. Specifically, the first embodiment of the present invention relates to a target nucleic acid concentration measuring system in which estimation accuracy is improved by a procedure for estimating a size of each of particles through use of the center positions of the particles and the vicinal relationship thereof without using a particle contour, and a concentration estimating procedure in which particle correction accuracy is improved by the Monte Carlo method.

Second Embodiment

Figure 18:
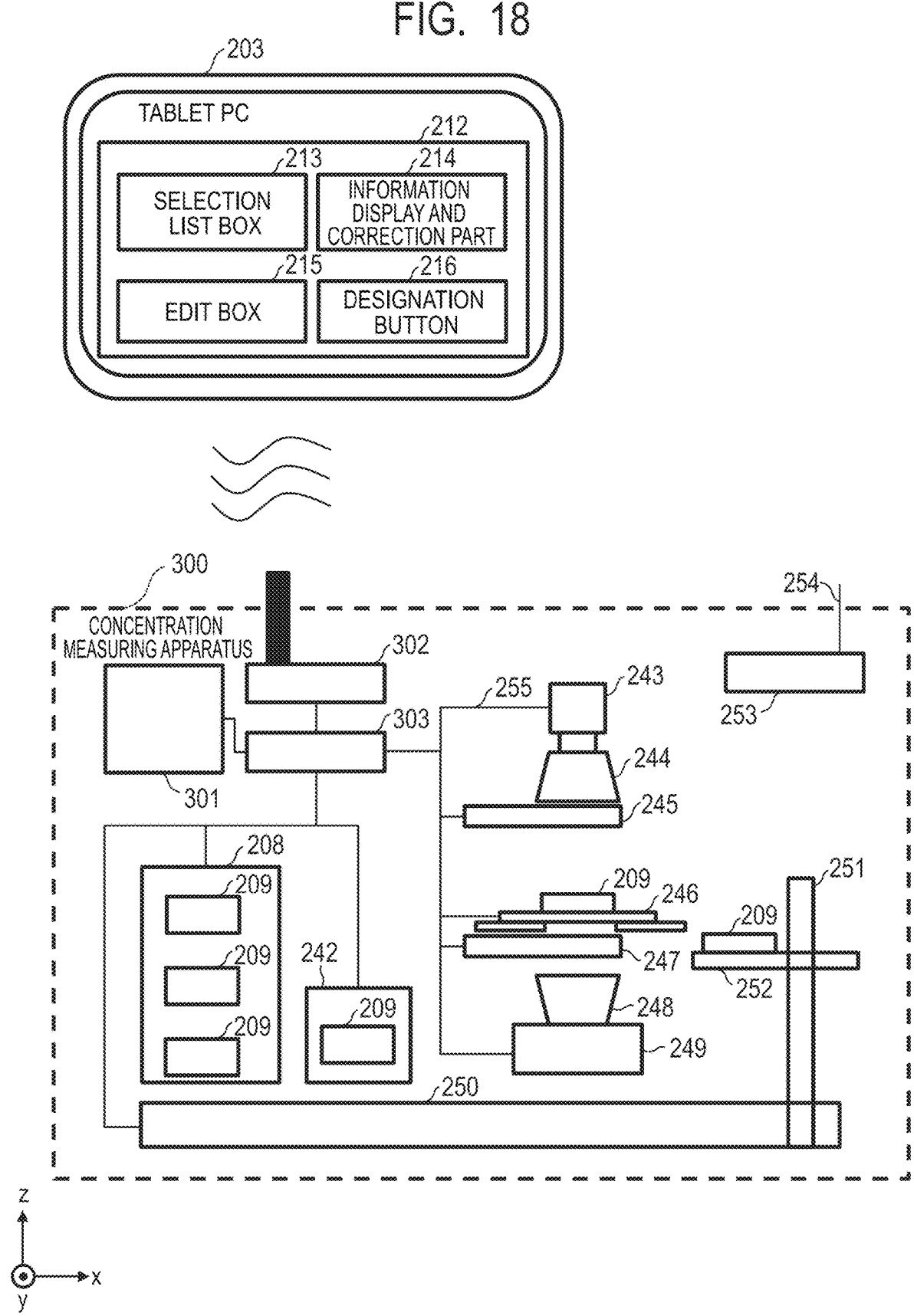
FIG. 18 is a diagram for illustrating one example of a configuration of a concentration measuring apparatus according to a second embodiment of the present invention.

A concentration measuring apparatus according to a second embodiment of the present invention is described with reference to FIG. 18. FIG. 18 is a diagram for illustrating one example of a configuration of a concentration measuring apparatus 300 according to the second embodiment. As illustrated in FIG. 18, the concentration measuring apparatus 300 according to the second embodiment has a configuration in which the functions of the image processing apparatus 202 and the wireless LAN router 206 are added to the imaging apparatus 201 of the concentration measuring system 200 according to the first embodiment. In terms of the functions, both the concentration measuring apparatus 300 and the concentration measuring system 200 are substantially the same. In the following, only the points different from those of the concentration measuring system 200 are described.

The concentration measuring apparatus 300 includes a wireless LAN interface 302 instead of the network interface 240 provided in the imaging apparatus 201. In order to implement the Web server function, which is performed by the image processing apparatus 202, the controller 303 can have, for example, a configuration such as that of a general-purpose PC including a CPU and a memory. The particle measuring method 010 and the target nucleic acid counting method 011 performed by the image processing apparatus 202 can be performed by an image processing board 301 instead.

Figure 19:
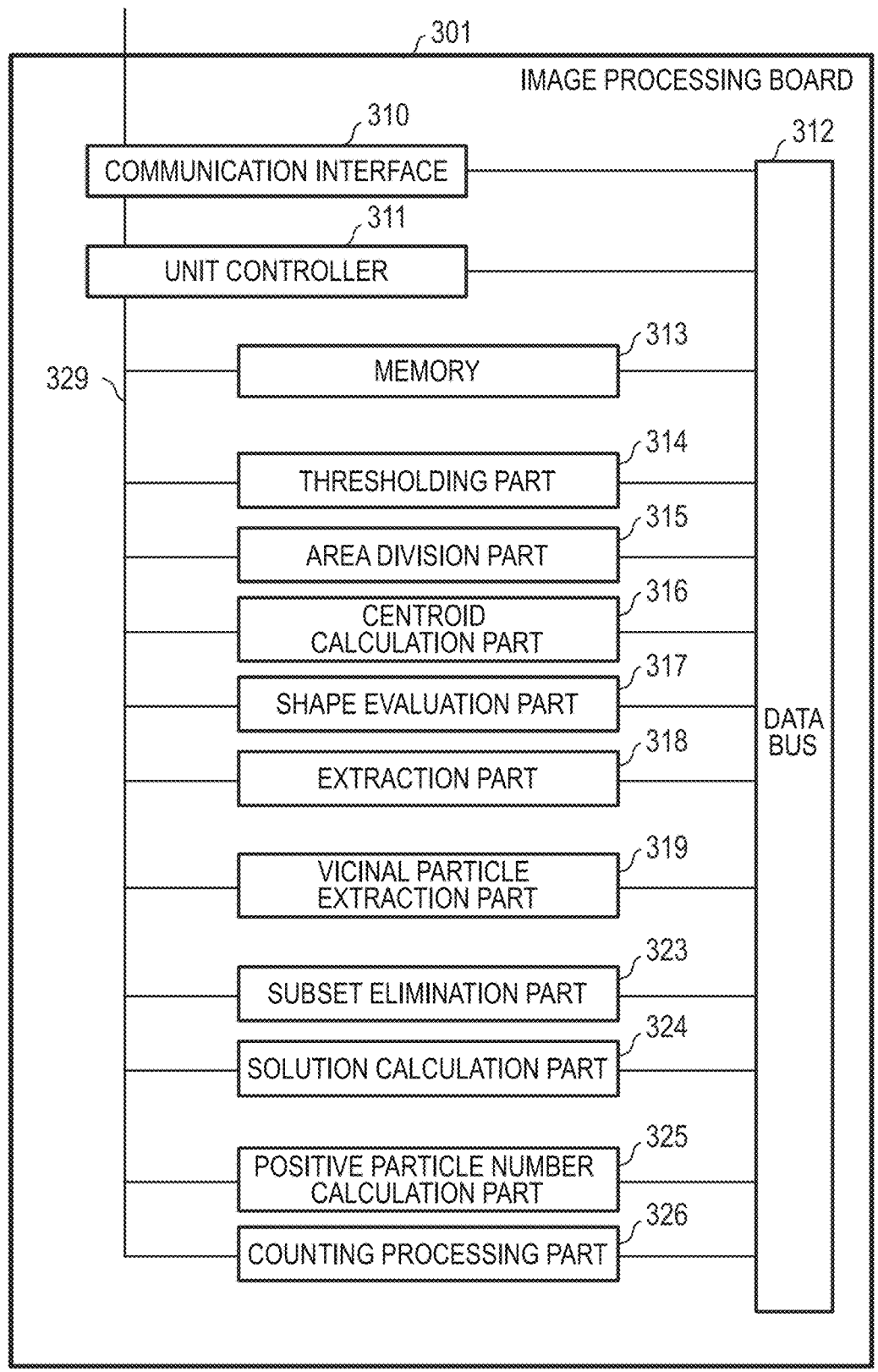
FIG. 19 is a block diagram for illustrating one example of a configuration of an image processing board provided in the concentration measuring apparatus according to the second embodiment.

Next, the configuration of the image processing board 301 is described with reference to FIG. 19. FIG. 19 is a block diagram for illustrating one example of a configuration of the image processing board 301 provided in the concentration measuring apparatus 300 according to the second embodiment. As illustrated in FIG. 19, the image processing board 301 includes a communication interface 310, a unit controller 311, a data bus 312, a memory 313, and various calculating units. The image processing board 301 includes, as the calculating units, a thresholding part 314, an area division part 315, a centroid calculation part 316, a shape evaluation part 317, an extraction part 318, a vicinal particle extraction part 319, a subset elimination part 323, a solution calculation part 324, a positive particle number calculation part 325, and a counting processing part 326. Those calculating units perform a plurality of steps included in the particle measuring method 010 and the target nucleic acid counting method 011.

Next, the calculating units regarding the performance of the particle measuring method 010 illustrated in FIG. 2 in the second embodiment are described. The thresholding part 314, the area division part 315, the centroid calculation part 316, the shape evaluation part 317, and the extraction part 318 are the calculating units configured to perform five steps (see FIG. 3) forming the particle position acquisition step S100. The vicinal particle extraction part 319 is the calculating unit configured to perform the vicinal particle extraction step S101. The subset elimination part 323 and the solution calculation part 324 are the calculating units configured to perform two steps (see FIG. 8) forming the calculation step S102.

The calculating units responsible for performing the target nucleic acid counting method 011 illustrated in FIG. 10 in the second embodiment are described. The positive particle number calculation part 325 is the calculating unit configured to perform the positive particle number calculation step S160. The counting processing part 326 is the calculating unit configured to perform the counting step S161.

Next, data exchange to be performed between constituent elements of the image processing board 301 is described. Calculation start designation sent from the controller 303 is sent to the unit controller 311 through the communication interface 310. Simultaneously, image data to be calculated and the like are sent from the controller 303 to the memory 313 through the data bus 312 and held in the memory 313. The unit controller 311 performs execution start designation and end confirmation for the calculating unit. Further, the unit controller 311 also performs assignment processing (mediation processing) for synchronous signal information (clock of the data bus 312) for preventing interference between the calculating units. Specifically, the unit controller 311 sends calculation start designation and assigned synchronous signal information to a set of a calculating unit that starts calculation and the memory 313 through a controller-unit communication channel 329.

The calculating unit performs calculation on image data held in the memory 313 and data in a numerical value array generated at a time of calculation while reading and correcting the data. The calculating unit sends end confirmation information to the unit controller 311 at a time of completion of calculation. The unit controller 311 repeatedly sends the execution start designation to a calculating unit that performs a subsequent calculation step after receiving the end confirmation information. The unit controller 311 sends the obtained concentration information to the controller 303 after performing the entire processing of the particle measuring method 010 and the target nucleic acid counting method 011.

Regarding the details of the processing to be performed in the concentration measuring apparatus 300, there is one point different from that of the concentration measuring system 200. The processing ability of the image processing board 301 of the concentration measuring apparatus 300 is lower than that of the image processing apparatus 202 in some cases. Large image data cannot be handled, and hence it is difficult to improve accuracy of the particle measuring method 010. In view of the foregoing, in the counting processing part 326, an average value of sizes of particles, which are statistically measured, can be used as a reference value in order to prevent an excessive decrease in accuracy.

As described above, the second embodiment of the present invention relates to a target nucleic acid concentration measuring apparatus, which achieves correction of a variation in particle even when it is difficult to acquire a particle volume by imaging, for example, due to the influence of a depth of field. In addition, the second embodiment of the present invention relates to a target nucleic acid concentration measuring apparatus, which has an image processing function therein, and can be used also in a place in which network connection is difficult.

Third Embodiment

Figure 20:
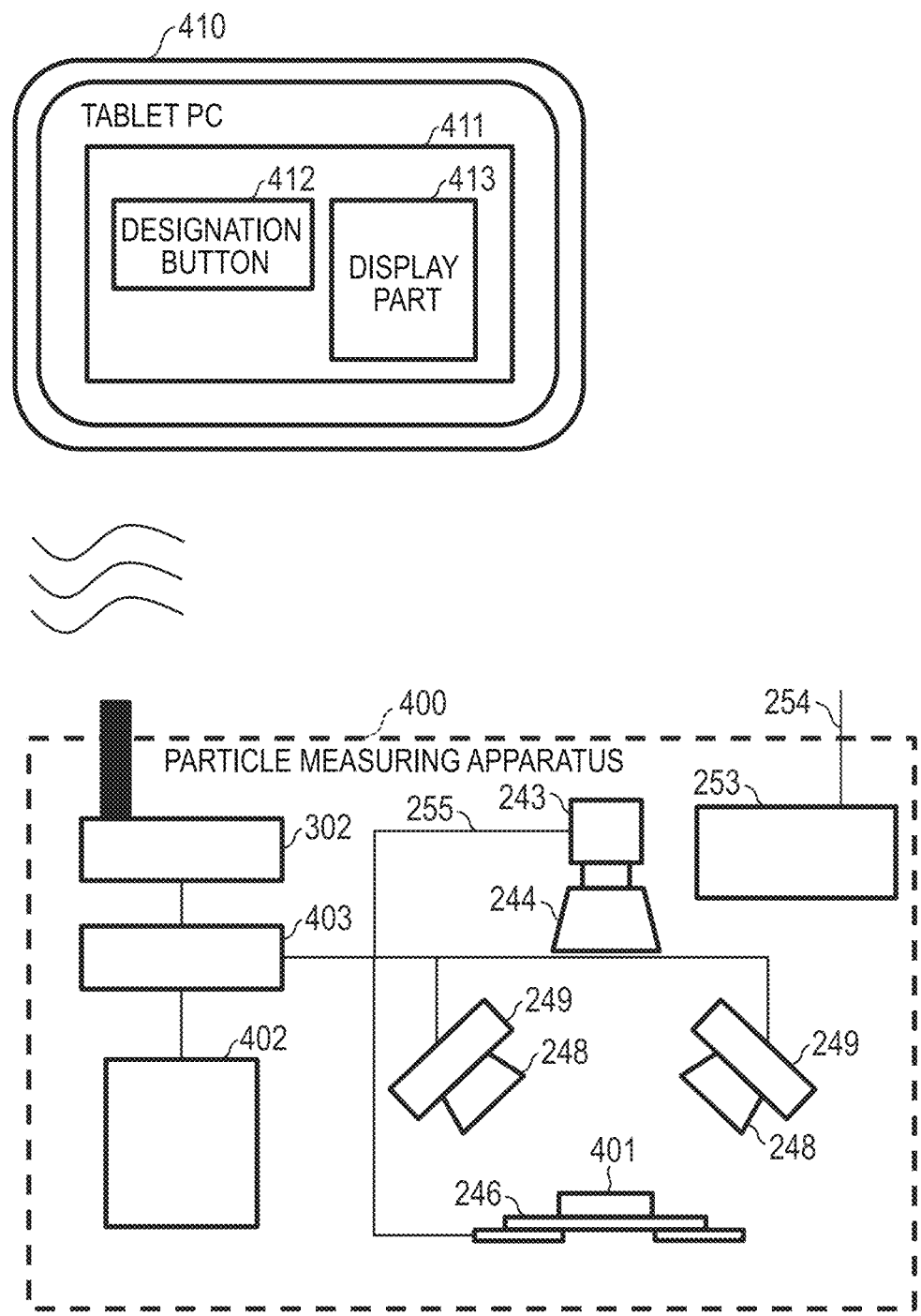
FIG. 20 is a diagram for illustrating one example of a configuration of a particle measuring apparatus according to a third embodiment of the present invention.

A particle measuring apparatus according to a third embodiment of the present invention is described with reference to FIG. 20. FIG. 20 is a diagram for illustrating one example of a configuration of a particle measuring apparatus 400 according to the third embodiment. As illustrated in FIG. 20, the particle measuring apparatus 400 according to the third embodiment is an apparatus in which the function of the concentration measuring apparatus 300 according to the second embodiment is eliminated, and only the particle measurement function is left. In addition, it is assumed that a particle to be measured by the particle measuring apparatus 400 emits scattered light from a surface or an inside of the particle in response to illumination light. For example, when a colored particle or an opaque or semitransparent object such as a ball, a bean, fish roe, or a tablet is inspected, scattered light is measured. In particle image data obtained from the scattered light, there is no density difference in a center portion and a peripheral portion of the particle, and the entire particle becomes light, with the result that a pixel corresponding to oil between the particles becomes dark. In this case, in the extraction step S114 of the particle position acquisition step S100, it is not required to remove a white area between the particles. In addition, there is no white area between the particles, and hence the procedure illustrated in FIG. 7A is adopted as the vicinal particle extraction step S101.

Only the differences from the concentration measuring apparatus 300 are described. Unlike the inspection plate 209, an inspection plate 401 handled by the particle measuring apparatus 400 may not have a particle generation function, and it is only required that the inspection plate 401 be a container configured to accommodate the particles on a surface. Unlike the image processing board 301, an image processing board 402 does not have the calculating units required for performing the target nucleic acid counting method 011, and may be specialized in only particle measurement. A controller 403 may be a controller obtained by omitting control procedures other than those of the camera 243, the LED light source 249, the xy stage 246, and the image processing board 402 from the controller 303. In addition, a management screen 411 of a tablet PC 410 is configured to manage the particle measuring apparatus 400, and may have a simple configuration including a designation button 412 configured to designate start and end of imaging and a display part 413 configured to display situation and results of measurement.

As described above, the third embodiment of the present invention relates to a particle measuring apparatus, which achieves measurement of a size of each of particles even under a situation in which it is difficult to acquire a particle volume by imaging, for example, due to the influence of a depth of field. In addition, unlike the other embodiments, the third embodiment of the present invention relates to a particle measuring apparatus, which achieves measurement of a size of each of particles through use of scattered light from the particles.

In the above, the preferred embodiments of the present invention are described in detail, but the present invention is not limited to the above-mentioned specific embodiments, and various modifications and changes may be made within the gist of the present invention described in the appended claims.

The particle measuring method, the particle measuring apparatus, and the nucleic acid concentration measuring system according to at least one embodiment of the present invention can be widely used in measurement of minute particles and measurement of a nucleic acid concentration, and in particular, are useful for measurement in pathological examination in the medical field.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-125435, filed Jun. 29, 2018, which is hereby incorporated by reference herein in its entirety.

What is claimed is:

1. A particle measuring method for measuring, based on image data containing an image of a plurality of particles, a size of each of the plurality of particles included in the image data, the particle measuring method comprising:
acquiring a position of each of the plurality of particles from the image data;
extracting a plurality of particles vicinal to each other in the image data; and
calculating the size of each of the plurality of particles based on a distance between the plurality of particles vicinal to each other, which are extracted in the extracting a plurality of particles vicinal to each other,
wherein the calculating the size of each of the plurality of particles includes solving a simultaneous equation representing a relationship between a distance between vicinal particles obtained in the extracting a plurality of particles vicinal to each other and a size of each of the vicinal particles, to thereby calculate the size of each of the vicinal particles, and
wherein the calculating the size of each of the plurality of particles includes:
selecting, from vicinal particles obtained in the extracting a plurality of particles vicinal to each other, a subset of the vicinal particles;
acquiring a number of the vicinal particles included in the subset and a number of particle pairs having a vicinal relationship; and
eliminating, when the number of the vicinal particles is larger than the number of the particle pairs, a plurality of coefficients related to the vicinal particles included in the subset from the simultaneous equation.

2. The particle measuring method according to claim 1, wherein the size of each of the plurality of particles includes any one of sizes selected from the group consisting of a diameter, a sectional area, and a volume of a sphere containing one of the plurality of particles.

3. The particle measuring method according to claim 1, wherein the size of each of the plurality of particles includes any one of sizes selected from the group consisting of a diameter, a sectional area, and a volume of each of the plurality of particles having a spherical shape.

4. The particle measuring method according to claim 1, wherein the acquiring a position of each of the plurality of particles includes:
   a thresholding step of classifying pixels in the image data into one of: first pixels each representing a center portion and an interparticle area of the plurality of particles; and second pixels each representing a peripheral portion and the interparticle area of the plurality of particles;
   an area division step of extracting a partial area formed of only the first pixels;
   a shape evaluation step of calculating a shape evaluation value representing a shape of the partial area;
   an extraction step of extracting a particle area, which is a partial area representing the center portion of each of the plurality of particles, based on the shape evaluation value; and
   a centroid calculation step of calculating a centroid position of the pixels in the particle area as a particle position.

5. The particle measuring method according to claim 4, wherein the extracting a plurality of particles vicinal to each other includes:
   selecting two particle areas; and
   extracting the two particle areas as vicinal particles when the first pixels located on a line connecting particle positions in the two selected particle areas belong to only the two selected particle areas.

6. The particle measuring method according to claim 4, wherein the extracting a plurality of particles vicinal to each other includes:
   selecting two particle areas;
   determining, on a line connecting particle positions in the two selected particle areas, for each of the two selected particle areas, a maximum distance of the first pixels belonging to the same particle area from a centroid of the particle area;
   determining a difference of a distance between the two particle positions from a sum of the maximum distances; and
   extracting the two particle areas as vicinal particles when the first pixels located on the line connecting the particle positions in the two selected particle areas belong to only the two selected particle areas, and the difference of the distance is smaller than half a distance between the two particle positions.

7. A particle measuring apparatus, which is configured to measure, based on an image of a specimen including a plurality of particles, a size of each of the plurality of particles included in the image,
   the particle measuring apparatus comprising:
   an imaging unit configured to image the specimen;
   a particle position acquiring unit configured to acquire a position of each of the plurality of particles from image data obtained by the imaging unit;
   a vicinal particle extracting unit configured to extract a plurality of particles vicinal to each other; and a calculating unit configured to calculate the size of each of the plurality of particles based on a distance between one of the plurality of particles and another of the plurality of particles that is vicinal to the one of the plurality of particles,
wherein the calculating the size of each of the plurality of particles includes solving a simultaneous equation representing a relationship between a distance between vicinal particles obtained in the extracting a plurality of particles vicinal to each other and a size of each of the vicinal particles, to thereby calculate the size of each of the vicinal particles, and
wherein the calculating the size of each of the plurality of particles includes:
   selecting, from vicinal particles obtained in the extracting a plurality of particles vicinal to each other, a subset of the vicinal particles;
   acquiring a number of the vicinal particles included in the subset and a number of particle pairs having a vicinal relationship; and
   eliminating, when the number of the vicinal particles is larger than the number of the particle pairs, a plurality of coefficients related to the vicinal particles included in the subset from the simultaneous equation.

8. A particle measuring apparatus, which is configured to measure, based on an image of a specimen including a plurality of particles, a size of each of the plurality of particles included in the image,
   the particle measuring apparatus comprising:
   an input unit configured to receive input of a reference value of the size of each of the plurality of particles;
   an imaging unit configured to image the specimen;
   a particle position acquiring unit configured to acquire a position of each of the plurality of particles from image data obtained by the imaging unit;
   a vicinal particle extracting unit configured to extract a plurality of particles vicinal to each other;
   a first calculating unit configured to calculate a ratio of the size of each of the plurality of particles based on a distance between one of the plurality of particles and another of the plurality of particles that is vicinal to the one of the plurality of particles; and
   a second calculation unit configured to calculate the size of each of the plurality of particles based on the ratio and the reference value of the size,
wherein the calculating the size of each of the plurality of particles includes solving a simultaneous equation representing a relationship between a distance between vicinal particles obtained in the extracting a plurality of particles vicinal to each other and a size of each of the vicinal particles, to thereby calculate the size of each of the vicinal particles, and
wherein the calculating the size of each of the plurality of particles includes:
   selecting, from vicinal particles obtained in the extracting a plurality of particles vicinal to each other, a subset of the vicinal particles;
   acquiring a number of the vicinal particles included in the subset and a number of particle pairs having a vicinal relationship; and
   eliminating, when the number of the vicinal particles is larger than the number of the particle pairs, a plurality of coefficients related to the vicinal particles included in the subset from the simultaneous equation.

* * * * *